(12) United States Patent
Claremon et al.

(10) Patent No.: US 8,835,426 B2
(45) Date of Patent: Sep. 16, 2014

(54) CYCLIC UREA AND CARBAMATE INHIBITORS OF 11β-HYDROXYSTEROID DEHYDROGENASE 1

(75) Inventors: David A. Claremon, Maple Glenn, PA (US); Gerard McGeehan, Garnet Valley, PA (US); Suresh B. Singh, Kendall Park, NJ (US); Colin M. Tice, Maple Glen, PA (US); Yuanjie Ye, Ambler, PA (US); Wei Zhao, Eagleville, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 857 days.

(21) Appl. No.: 12/449,752

(22) PCT Filed: Feb. 26, 2008

(86) PCT No.: PCT/US2008/002517
§ 371 (c)(1),
(2), (4) Date: Apr. 12, 2010

(87) PCT Pub. No.: WO2008/106128
PCT Pub. Date: Sep. 4, 2008

(65) Prior Publication Data
US 2010/0197675 A1   Aug. 5, 2010

Related U.S. Application Data

(60) Provisional application No. 60/903,473, filed on Feb. 26, 2007.

(51) Int. Cl.
| | | |
|---|---|---|
| A61K 31/421 | (2006.01) | |
| C07D 263/22 | (2006.01) | |
| C07D 263/24 | (2006.01) | |
| A61K 31/535 | (2006.01) | |
| C07D 265/10 | (2006.01) | |
| C07D 233/34 | (2006.01) | |
| C07D 239/10 | (2006.01) | |
| C07D 401/10 | (2006.01) | |
| C07D 267/06 | (2006.01) | |
| C07D 413/10 | (2006.01) | |
| C07D 233/32 | (2006.01) | |

(52) U.S. Cl.
CPC ............ C07D 263/22 (2013.01); C07D 233/34 (2013.01); C07D 263/24 (2013.01); C07D 401/10 (2013.01); C07D 265/10 (2013.01); C07D 267/06 (2013.01); C07D 413/10 (2013.01); C07D 239/10 (2013.01); C07D 233/32 (2013.01)
USPC ........ 514/228.8; 514/256; 514/392; 514/376; 544/315; 544/97; 548/316.4; 548/229

(58) Field of Classification Search
CPC .. C07D 233/34; C07D 239/10; C07D 263/22; C07D 263/24; C07D 265/10
USPC ................ 514/256, 392, 228.8; 544/315, 97; 548/316.4, 229
See application file for complete search history.

(56) References Cited

U.S. PATENT DOCUMENTS

| | | |
|---|---|---|
| 3,341,538 A | 9/1967 | Block et al. |
| 3,681,349 A | 8/1972 | Schwan et al. |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |

(Continued)

FOREIGN PATENT DOCUMENTS

| | | |
|---|---|---|
| DE | 1801556 A1 | 5/1970 |
| DE | 19918725 A1 | 10/2000 |

(Continued)

OTHER PUBLICATIONS

Chemical Abstracts, Registry No. 351443-37-3 (available on Aug. 15, 2001).*

(Continued)

*Primary Examiner* — Andrew D Kosar
*Assistant Examiner* — Valerie Rodriguez-Garcia
(74) *Attorney, Agent, or Firm* — McCarter & English LLP; Steven G. Davis; Michael J. DeGrazia

(57) ABSTRACT

This invention relates to novel compounds of the Formula (I),

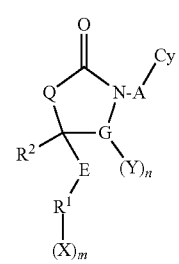

pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds of the Formula (I) and methods for their use in the reduction or control of the production of cortisol in a cell or the inhibition of the conversion of cortisone to cortisol in a cell.

15 Claims, No Drawings

(56) References Cited

U.S. PATENT DOCUMENTS

| | | | |
|---|---|---|---|
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 7,026,310 B2 | 4/2006 | Emig et al. |
| 7,056,912 B2 | 6/2006 | Emig et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0124384 A1 | 5/2008 | Blum |
| 2008/0188482 A1 | 8/2008 | Rice et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0264650 A1 | 10/2009 | Cho et al. |
| 2010/0041637 A1 | 2/2010 | Claremon et al. |

FOREIGN PATENT DOCUMENTS

| | | |
|---|---|---|
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0928789 A1 | 7/1999 |
| EP | 1156049 A | 11/2001 |
| EP | 1270724 A2 | 1/2003 |
| EP | WO 2006/066924 | * 6/2006 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | WO 97/36605 | 10/1997 |
| WO | WO 98/57940 | 12/1998 |
| WO | WO 99/05125 | 2/1999 |
| WO | WO 99/06395 | 2/1999 |
| WO | WO 01/00595 A1 | 1/2001 |
| WO | WO 01/44200 A2 | 6/2001 |
| WO | WO 01/55063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | WO 2005/113525 A1 | 12/2005 |
| WO | WO 2006/003494 A2 | 1/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | WO 2006/104280 A | 10/2006 |
| WO | WO 2007/008529 A2 | 1/2007 |
| WO | WO 2007/022371 | * 2/2007 |
| WO | WO 2007/051810 | 5/2007 |
| WO | WO 2007/061661 A2 | 5/2007 |
| WO | WO 2007/068330 A1 | 6/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A | 7/2007 |
| WO | WO 2007/084314 A2 | 7/2007 |
| WO | WO 2007/109456 A2 | 9/2007 |
| WO | WO 2007/118185 A2 | 10/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |

(56) References Cited

FOREIGN PATENT DOCUMENTS

| WO | WO 2008/000951 | 1/2008 |
| --- | --- | --- |
| WO | WO 2008/031227 A1 | 3/2008 |
| WO | WO 2008/036715 A1 | 3/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | WO 2009/117109 | 9/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | WO 2010/091067 | 8/2010 |
| WO | WO 2010/127237 | 11/2010 |

OTHER PUBLICATIONS

Souillac et al., Characterization of Delivery Systems, Differential Scanning Calorimetry, pp. 217-218 (in Encyclopedia of Controlled Drug Delivery, 1999, John Wiley & Sons, pp. 212-227).*
Morissette et al. Advanced Drug Delivery Reviews 2004, 56, 275-300.*
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
International Search Report—(PCT/US2010/023021) Date of Mailing Aug. 5, 2010.
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Sugery, 2000, vol. 127, pp. 687-695.
Database Caplus [Online] Chemical Abstracts Service, Maillard et al., "Spiroheterocyclic Cycloalkane Compounds, II. Synthesis of 6-Substituted-Tetrahydro-2H-1,3-Oxazine-2-Ones", XP002516521, retrieved from STN Database accession No. 1969:68280 CAS RN: 20057-45-8 abstract, (1969).
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract, (1978).
Zhurnal Organicheskoi Khimii, 1978, vol. 14(5), pp. 1092-1094.
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 522 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Aiphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.

(56) References Cited

OTHER PUBLICATIONS

Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon—Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)- Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.

* cited by examiner

CYCLIC UREA AND CARBAMATE INHIBITORS OF 11β-HYDROXYSTEROID DEHYDROGENASE 1

RELATED APPLICATIONS

This application is the U.S. National Stage of International Application No. PCT/US2008/002517, filed Feb. 26, 2008, which designates the U.S., published in English, and claims the benefit of U.S. Provisional Application No. 60/903,473, filed Feb. 26, 2007. The entire teachings of the above applications are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-NSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4th Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844). Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression.

There is also evidence that glucocorticoids and 11β-HSD1 play a role in regulation of in intra-ocular pressure (IOP) (Stokes et al. (2000) Invest. Opthalmol. Vis. Sci. 41: 1629-1683; Rauz et al. (2001) Invest. Opthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat or prevent glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders.

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

As evidenced herein, there is a continuing need for new and improved drugs that inhibit 11β-HSD1. The novel compounds of the instant invention are effective inhibitors of 11β-HSD1.

SUMMARY OF THE INVENTION

The present invention provides, inter alia, compounds of Formula I or pharmaceutically acceptable salts or prodrugs thereof, wherein constituent members are defined herein as follows:

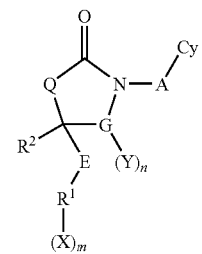

wherein:

Q is $NR^3$, O or S;

$R^1$ is selected from the group consisting of (1) H; or (2) ($C_1$-$C_8$)alkyl, ($C_3$-$C_7$)cycloalkyl, heterocyclyl, ($C_1$-$C_4$)alkoxy($C_1$-$C_4$)alkyl, ($C_1$-$C_4$)alkylthio($C_1$-$C_4$)alkyl, ($C_1$-$C_4$)alkylsulfinyl($C_1$-$C_4$)alkyl, and ($C_1$-$C_4$)alkylsulfonyl($C_1$-$C_4$)alkyl; or (3) phenyl, phenyl($C_1$-$C_4$)alkyl, heteroaryl, and heteroaryl($C_1$-$C_4$)alkyl;

X is independently selected from the group consisting of halogen, OH, $CH_2OH$, ($C_1$-$C_3$)alkyl, ($C_1$-$C_3$)haloalkyl, OR*, O(($C_1$-$C_3$)haloalkyl), CN, $CH_2CN$, $NO_2$, $CH_2NO_2$, SH, SR*, $SO_2H$, $CH_2SO_2H$, $SO_2R$*, $CH_2SO_2R$*, $SO_2NH_2$, $SO_2NHR$*, $SO_2NR$*$_2$, $CH_2SO_2NH_2$, $CH_2SO_2NHR$*, $CH_2SO_2NR$*$_2$, $SO_2CF_3$, $CH_2SO_2CF_3$, $CONH_2$, $CONHR$*, $CONR$*$_2$, $CH_2CONH_2$, $CH_2CONHR$*, $CH_2CONR$*$_2$, $CO_2H$, $CH_2CO_2H$, $NH_2$, $NHR$*, $NR$*$_2$, ($C_1$-$C_3$)alkyl($NH_2$), ($C_1$-$C_3$)alkyl($NHR$*), ($C_1$-$C_3$)alkyl($NR$*$_2$), aryl, heteroaryl and additionally $SO_3H$, $CH_2SO_3H$ and heterocyclyl optionally substituted with alkyl, haloalkyl, hydroxy or oxo;

additionally, when $R^1$ is heterocyclyl or heteroaryl, X can also be oxo, such that a carbonyl group or an N-oxide is formed;

m is 0, 1, 2 or 3;

$R^2$ and $R^3$ are independently selected from the group consisting of (1) H; or (2) ($C_1$-$C_8$)alkyl, ($C_3$-$C_7$)cycloalkyl, heterocyclyl, ($C_1$-$C_4$)alkoxy($C_1$-$C_4$)alkyl, ($C_1$-$C_4$)alkylthio($C_1$-$C_4$)alkyl, ($C_1$-$C_4$)alkylsulfinyl($C_1$-$C_4$)alkyl, ($C_1$-$C_4$)alkylsulfonyl($C_1$-$C_4$)alkyl optionally substituted with one to three substituents independently selected from the group consisting of halogen, OH, (═O), $CONH_2$, $CO_2H$, $COCH_3$, $C(O)_2CH_3$, $NH_2$, $NHR$*, $NR$*$_2$, aryl, heteroaryl and additionally cyano, OR*, SR*, S(═O)R*, S(═O)$_2$R*, OP(=O)(OH)$_2$, NHSO$_2$R*, NR*SO$_2$R*, NHC(=O)R*, NR*C(=O)R*, NHC(=O)OR*, NR*C(=O)OR*, NHC(=O)NH$_2$, NHC(=O)NHR*, NHC(=O)N(R*)$_2$, NR*C(=O)NH$_2$, NR*C(=O)NHR*, NR*C(=O)N(R*)$_2$, OC(=O)NH$_2$, OC(=O)NHR*, OC(=O)N(R*)$_2$, NHS(=O)$_2$OR*, NR*S(=O)$_2$OR*, NHS(=O)$_2$NH$_2$, NHS(=O)$_2$NHR*, NHS(=O)$_2$N(R*)$_2$, NR*S(=O)$_2$NH$_2$, NR*S(=O)$_2$NHR*, NR*S(=O)$_2$N(R*)$_2$, OS(=O)$_2$NH$_2$, OS(=O)$_2$NHR*, OS(=O)$_2$N(R*)$_2$, heterocyclyl; or (3) phenyl, phenyl(C$_1$-C$_4$)alkyl, heteroaryl, heteroaryl(C$_1$-C$_4$)alkyl optionally substituted with one to three substituents independently selected from the group consisting of OH, CH$_2$OH, (C$_1$-C$_3$)alkyl, (C$_1$-C$_3$)haloalkyl, OR*, O((C$_1$-C$_3$)haloalkyl), CN, CH$_2$CN, NO$_2$, CH$_2$NO$_2$, SH, SR*, SO$_2$H, CH$_2$SO$_2$H, SO$_2$R*, CH$_2$SO$_2$R*, SO$_2$NH$_2$, SO$_2$NHR*, SO$_2$NR*$_2$, CH$_2$SO$_2$NH$_2$, CH$_2$SO$_2$NHR*, CH$_2$SO$_2$NR*$_2$, SO$_2$CF$_3$, CH$_2$SO$_2$CF$_3$, CONH$_2$, CONHR*, CONR*$_2$, CH$_2$CONH$_2$, CH$_2$CONHR*, CH$_2$CONR*$_2$, CO$_2$H, CH$_2$CO$_2$H, NH$_2$, NHR*, NR*$_2$, (C$_1$-C$_3$)alkyl(NH$_2$), (C$_1$-C$_3$)alkyl(NHR*), (C$_1$-C$_3$)alkyl(NR*$_2$), aryl, heteroaryl, and additionally—SO$_3$H and CH$_2$SO$_3$H;

provided that
1) R$^1$ and R$^2$ are not both hydrogen when E is a bond; and
2) R$^1$ is not hydrogen when m is greater than 0;
each R* is independently C$_1$-C$_3$ alkyl;
E is a bond, CH$_2$, CHMe, CMe$_2$, CH$_2$CH$_2$, OCH$_2$, OCHMe, OCMe$_2$, SCH$_2$, SCHMe, SCMe$_2$, provided that O and S are attached to R$^1$;
G is a 1, 2, or 3 carbon alkylene chain;
Y is independently selected from the group consisting of halogen, (C$_1$-C$_3$)alkyl, CF$_3$, CONH$_2$, CH$_2$CONH$_2$, CO$_2$H, CH$_2$CO$_2$H, (C$_1$-C$_3$)alkylamino(C$_1$-C$_3$)alkyl and di(C$_1$-C$_3$)alkylamino(C$_1$-C$_3$)alkyl;
n is 0, 1, 2 or 3;
A is a bond, CH$_2$, CHMe, CMe$_2$, or CH$_2$CH$_2$;
Cy is (C$_7$-C$_{12}$)bicycloalkyl or (C$_9$-C$_{12}$)tricycloalkyl in which 1-2 carbon atoms are optionally replaced with heteroatoms independently selected from N and O, and which is optionally substituted with 1-3 groups independently selected from halogen, cyano, (C$_1$-C$_3$)alkyl, halo(C$_1$-C$_3$)alkyl, hydroxy, hydroxy(C$_1$-C$_3$)alkyl, amino, (C$_1$-C$_4$)acylamino, (C$_1$-C$_3$)alkylsulfonylamino, CH$_2$CH$_2$CO$_2$H, (C$_1$-C$_3$)alkylcarbamoyl, di(C$_1$-C$_3$)alkylcarbamoyl, (C$_1$-C$_3$)alkylaminosulfonyl, di(C$_1$-C$_3$)alkylaminosulfonyl, optionally substituted aryl, optionally substituted heteroaryl, oxo-substituted heteroaryl, amino-substituted heteroaryl, heterocyclyl, oxo-substituted heterocyclyl and C(=NOH)NH$_2$, CON(R$^4$)$_2$, CH$_2$CON(R$^4$)$_2$, SO$_2$N(R$^4$)$_2$, CO$_2$R$^4$, CH$_2$CO$_2$R$^4$, SO$_2$R$^4$, NR$^4$COR$^4$, NR$^4$CO$_2$R$^4$, NR$^4$SO$_2$R$^4$, and additionally OC(=O)N(R$^4$),
wherein each R$^4$ is independently hydrogen, (C$_1$-C$_{10}$) alkyl, aryl or aralkyl, or an enantiomer, diastereomer, geometrical isomer or pharmaceutically acceptable salt thereof.

Preferably, for the compounds of Formula I, Q is O or NR$^3$, and the values of the remaining variables are as described in Formula (I) More preferably, Q is NH or NMe, R$^1$ is (C$_1$-C$_6$)alkyl, (C$_3$-C$_7$)cycloalkyl or phenyl, R$^2$ is Me, G(Y)$_n$ is CH$_2$ or CH$_2$CH$_2$ and Cy is 1-adamantyl, 2-adamantyl, 1-hydroxy-4-adamantyl, 1-hydroxymethyl-4-adamantyl, or 1-carbamoyl-4-adamantyl and the values of the remaining variables are as described in Formula (I). Alternatively, Q is O, R$^1$ is (C$_1$-C$_6$)alkyl, (C$_3$-C$_7$)cycloalkyl or phenyl, R$^2$ is Me, G(Y)$_n$ is CH$_2$ or CH$_2$CH$_2$ and Cy is 1-adamantyl, 2-adamantyl, 1-hydroxy-4-adamantyl, 1-hydroxymethyl-4-adamantyl, or 1-carbamoyl-4-adamantyl and the values of the remaining variables are as described in Formula (I).

In another preferred embodiment, the invention is a compound of Formula I, wherein n is 0, and E is a bond and the values of the remaining variables are as described above. More preferably, R$^1$ is tert-butyl.

In another embodiment, the invention is a compound of Formula I, wherein E is a bond, R$^1$ is phenyl, X is fluorine and m is 0, 1 or 2, and values for the remainder of the variables are as described above for Formula (I).

In another embodiment, the invention is a compound of Formula I, wherein E is a bond, R$^1$ is phenyl, X is monofluorophenyl or difluorophenyl and m is 1, and values for the remainder of the variables are as described above for Formula (I).

In another embodiment, the invention is a compound of Formula I, wherein E is a bond, R$^1$ is phenyl, X is optionally substituted pyridyl or X is an oxo-substituted heterocyclyl optionally further substituted with alkyl, haloalkyl or hydroxy and m is 1, and values for the remainder of the variables are as described above for Formula (I)

In another embodiment, the invention is a compound of Formula I, wherein R$^2$ is hydroxy(C$_2$-C$_5$)alkyl, ω-H$_2$NC(=O)(C$_1$-C$_3$)alkyl, ω-MeSO$_2$NH(C$_1$-C$_3$)alkyl or 2-(4-morpholino)ethyl, and values for the remainder of the variables are as described above for Formula (I)

In another preferred embodiment, the invention is a compound of Formula I wherein:

Q is NR$^3$, or O;
R$^3$ is H, or (C$_1$-C$_6$)alkyl;
E is a bond, CH$_2$, CHMe, CMe$_2$, or CH$_2$CH$_2$;
R$^1$ is H, (C$_1$-C$_8$)alkyl, (C$_3$-C$_7$)cycloalkyl, phenyl, phenyl(C$_1$-C$_4$)alkyl, heteroaryl, or heteroaryl(C$_1$-C$_4$)alkyl;
X is F, Cl, Br, CN, OH, (C$_1$-C$_3$)alkyl, halo(C$_1$-C$_3$)alkyl, (C$_1$-C$_3$)alkoxy, (C$_1$-C$_3$)alkylsulfonyl, or CONH$_2$;
m is 0, 1, 2 or 3;
R$^2$ is H, Me, or CH$_2$OH;
provided that
1) R$^1$ and R$^2$ are not both hydrogen when E is a bond; and
2) R$^1$ is not hydrogen when m is greater than 0;
G(Y)$_n$ is CH$_2$, CH(C$_1$-C$_3$)alkyl, C((C$_1$-C$_3$)alkyl)$_2$, or CH$_2$CH$_2$;
n is 0, 1 or 2;
A is a bond, CH$_2$;
Cy is (C$_7$-C$_{12}$)bicycloalkyl and (C$_9$-C$_{12}$)tricycloalkyl in which 1-2 carbon atoms are optionally replaced with heteroatoms independently selected from N and O, and which is optionally substituted with 1-3 groups independently selected from halogen, cyano, (C$_1$-C$_3$)alkyl, halo(C$_1$-C$_3$)alkyl, hydroxy, hydroxy(C$_1$-C$_3$)alkyl, amino, (C$_1$-C$_4$)acylamino, (C$_1$-C$_3$)alkylsulfonylamino, CH$_2$CH$_2$CO$_2$H, (C$_1$-C$_3$)alkylcarbamoyl, di(C$_1$-C$_3$)alkylcarbamoyl, (C$_1$-C$_3$)alkylaminosulfonyl, di(C$_1$-C$_3$)alkylaminosulfonyl, optionally substituted aryl, optionally substituted heteroaryl, oxo-substituted heteroaryl, amino-substituted heteroaryl, heterocyclyl, oxo-substituted heterocyclyl and C(=NOH)NH$_2$, CON(R$^4$)$_2$, CH$_2$CON(R$^4$)$_2$, SO$_2$N(R$^4$)$_2$, CO$_2$R$^4$, CH$_2$CO$_2$R$^4$, SO$_2$R$^4$, NR$^4$COR$^4$, NR$^4$CO$_2$R$^4$, and NR$^4$SO$_2$R$^4$. Preferred values for Cy are 1-adamantyl, 2-adamantyl, 1-hydroxy-3-adamantyl, 1-(hydroxymethyl)-3-adamantyl, 1-carbamoyl-3-adamantyl, 1-hydroxy-4-adamantyl, 1-(hydroxymethyl)-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl;
each R$^4$ is independently hydrogen, (C$_1$-C$_{10}$) alkyl, aryl or aralkyl;
or an enantiomer, diastereomer, geometrical isomer or pharmaceutically acceptable salt thereof.

More preferably, $R^3$ is H or Me; E is a bond or methylene; $R^1$ is H, $(C_1-C_8)$alkyl, or $(C_3-C_7)$cycloalkyl; X is Cl, Br or OH; m is 0 or 1; $R^2$ is H, Me, or $CH_2OH$; $G(Y)_n$ is $CH_2$, $CHCH_3$, or $CH_2CH_2$; A is a bond or methylene; and Cy is 1-adamantyl, 2-adamantyl, 1-hydroxy-4-adamantyl, 1-hydroxymethyl-4-adamantyl, or 1-carbamoyl-4-adamantyl. The values of the remaining variables are as described above.

More preferred are compounds of Formula I wherein:

Q is $NR^3$, or O;

$R^3$ is H, or Me;

E is a bond, or $CH_2$;

$R^1$ is H, methyl, ethyl, isopropyl, isobutyl, tert-butyl, cyclohexyl, or Ph;

X is Cl, Br, or OH;

m is 0 or 1;

$R^2$ is H, Me, or $CH_2OH$;

$G(Y)_n$ is $CH_2$, CHMe, or $CH_2CH_2$;

n is 0 or 1;

A is a bond, or $CH_2$;

Cy is 1-adamantyl, 2-adamantyl, or 1-hydroxy-4-adamantyl;

or an enantiomer, diastereomer, geometrical isomer or pharmaceutically acceptable salt thereof.

Specifically preferred compounds of the Formula I are:

(S)-3((1-adamantyl)methyl)-5-phenyloxazolidin-2-one;
(S)-3((1-adamantyl)methyl)-5-isobutyloxazolidin-2-one;
(S)-3-(1-adamantyl)-5-isobutyloxazolidin-2-one;
(S)-3-(2-adamantyl)-5-isobutyloxazolidin-2-one;
(S)-3((1-adamantyl)methyl)-5-(2-chlorophenyl)oxazolidin-2-one;
(S)-3((1-adamantyl)methyl)-5-(t-butyl)oxazolidin-2-one;
(S)-3-(2-adamantyl)-5-tert-butyloxazolidin-2-one;
(S)-3-(2-adamantyl)-5-methyl-5-phenyloxazolidin-2-one;
(S)-3((1-adamantyl)methyl)-5-cyclohexyloxazolidin-2-one;
(S)-3-(2-adamantyl)-5-cyclohexyloxazolidin-2-one;
(R)-3-(2-adamantyl)-5-cyclohexyloxazolidin-2-one;
(4R,5S)-3-((1-adamantyl)methyl)-4-methyl-5-phenyloxazolidin-2-one;
(S)-1-(2-adamantyl)-4-tert-butylimidazolidin-2-one;
(S)-1-(2-adamantyl)-3-methyl-4-tert-butyl-imidazolidin-2-one;
5-(4-bromophenyl)-3-(2-adamantyl)oxazolidin-2-one;
(S)-1-(1-adamantyl)-4-phenylimidazolidin-2-one
4-tert-butyl-1-(2-adamantyl)tetrahydropyrimidin-2(1H)-one
(S)-4-cyclohexyl-1-(2-adamantyl)imidazolidin-2-one
(S)-4-isopropyl-1-(2-adamantyl)imidazolidin-2-one
5-(3-bromophenyl)-3-(2-adamantyl)oxazolidin-2-one
1-(2-adamantyl)-4-(hydroxymethyl)-4-isobutylimidazolidin-2-one
5-(biphenyl-3-yl)-3-(2-adamantyl)oxazolidin-2-one
5-(biphenyl-4-yl)-3-(2-adamantyl)oxazolidin-2-one or an enantiomer, diastereomer, geometrical isomer or pharmaceutically acceptable salts thereof.

The present invention further provides methods of inhibiting 11β-HSD1 by contacting 11β-HSD1 with a compound of Formula I of the invention.

The present invention further provides methods of inhibiting the conversion of cortisone to cortisol in a cell using a compound of Formula I of the invention.

The present invention further provides methods of inhibiting production of cortisol in a cell using a compound of Formula I of the invention.

The present invention further provides methods of increasing insulin sensitivity using a compound of Formula I of the invention.

The present invention further provides methods of preventing or treating diseases associated with activity of expression of 11β-HSD1 using a compound of Formula I of the invention.

DETAILED DESCRIPTION OF THE INVENTION

Definitions

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a saturated hydrocarbon ring having 3-8 carbon atoms and includes, for example, cyclopropyl, cyclobutyl, cyclopentyl, cyclohexyl, cycloheptyl, cyclooctyl, and the like.

The term "bicycloalkyl" means two saturated hydrocarbon rings having a total of 7-12 carbon atoms which are joined by 1,1-fusion, 1,2-fusion or 1,n-fusion to give spirocyclic ring systems, fused ring systems and bridged ring systems respectively. Spirocyclic ring systems include, for example, spiro[2.4]heptane, spiro[2.5]octane, spiro[4.4]nonane, spiro[4.5]decane, spiro[5.5]undecane and the like. Fused ring systems include, for example, bicyclo[4.1.0]heptane, octahydro-1H-indene, decahydronaphthalene and the like. Bridged ring systems include for example, bicyclo[3.3.1]nonane, bicyclo[2.2.2]octane, bicyclo[2.2.1]heptane and the like.

The term "tricycloalkyl" means three saturated hydrocarbon ring having a total of 9-12 carbon atoms which are joined by any combination of 1,1-fusion, 1,2-fusion or 1,n-fusion and includes, for example, adamantyl, noradamantyl and the like.

The terms "alkoxy" and "thioalkoxy" are O-alkyl or S-alkyl of from 1-6 carbon atoms.

The term "aryl" means an aromatic radical which is a phenyl group, a phenylalkyl group, a phenyl group substituted with 1-4 substituents selected from alkyl, alkoxy, thioalkoxy, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a ring containing 1-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-pyrazolyl, 2-, 4-, or 5-imidazolyl and the like optionally substituted by a substituent selected from alkyl, alkoxy, thioalkoxy, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide and azetidine. The term "oxo-substituted heterocyclyl" means a 4-, 5-, 6- and 7-membered saturated or partially unsaturated heterocyclic ring containing 1 to 4 heteroatoms independently selected from N, O, and S, and include pyrrolidin-2-one, piperidin-2-one, 1,2-dihydro-2-oxopyridine, 3,4-dihydro-4-oxopyrimidine, tetrahydropyrimidin-2(1H)-one. As such, a heterocyclyl substituted at a ring carbon with oxo forms a ketone at said position; and a heterocyclyl substituted at a ring nitrogen with oxo forms an n-oxide at said position. A heterocyclyl group can be optionally substituted with 1-4 substituents. Exemplary substituents include oxo, alkyl, haloalkyl and hydroxy.

The term "adamantyl" means an adamantane moiety bonded to another atom via the 1- or 2-position of adamantane. Examples of suitable adamantyl groups include 1-adamantyl, 2-adamantyl, 1-hydroxy-3-adamantyl, 1-(hydroxymethyl)-3-adamantyl, 1-carbamoyl-3-adamantyl, 1-hydroxy-4-adamantyl, 1-(hydroxymethyl)-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl;

The term "mammal" as used herein includes all mammals, including, but not limited to, humans.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts. Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
| --- | --- |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC.HCl, EDCl | 1-[3-(dimethylamino)propyl]-3-ethylcarbodiimide hydrochloride |
| Equiv | equivalents |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| Satd | saturated |
| SOCl$_2$ | thionyl chloride |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |

-continued

| Abbreviation | Meaning |
| --- | --- |
| Tlc, TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthesis

Compounds of the Formula I can be prepared by several processes. In the discussion below $R^1$-$R^3$, A, Cy, E, G, Q, X, Y, m and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In the first process a compound of Formula I can be prepared by reaction of an intermediate of Formula II with a reagent of Formula III, wherein $Z^1$ and $Z^2$ are leaving groups such as chloride, 1-imidazolyl or aryloxide in an inert solvent such as THF, CH$_2$Cl$_2$, toluene or MeCN, usually in the presence of an organic or inorganic base such as triethylamine or NaHCO$_3$ respectively, at −10° C. to 120° C.:

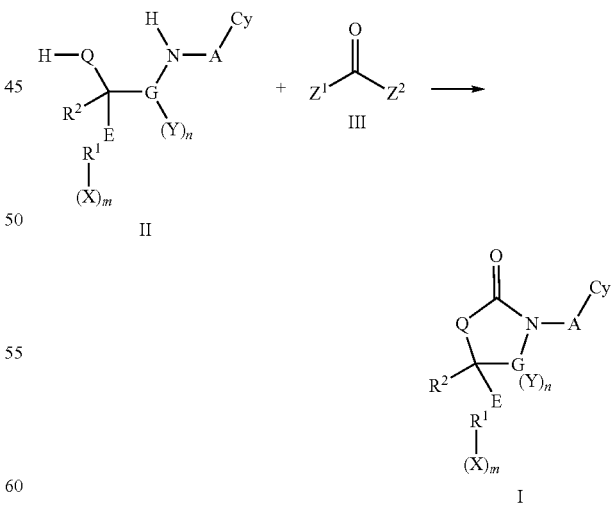

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both $OCCl_3$, III is triphosgene and as little as one third of molar equivalent can be used.

Intermediates of Formula II wherein Q is O, G is $CH_2$ and n is 0 can be prepared by reduction of amides of Formula IV using a hydride reagent such as $BH_3.THF$ solution, $BH_3.Me_2S$ or $LiAlH_4$ in an inert solvent ethereal such as THF or DME at 20° C. to 100° C. for between 1 h and 48 h:

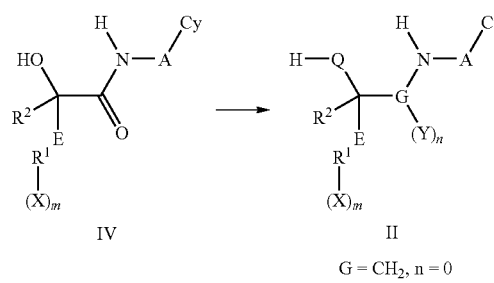

$G = CH_2, n = 0$

Intermediates of Formula IV can be prepared by coupling of an α-hydroxyacid of Formula V with an amine of Formula VI using standard peptide coupling reagents such as EDC in the presence of HOBt and N,N-diisopropylethylamine in an inert solvent such as $CH_2Cl_2$ at 0-30° C. for between 1 h and 24 h:

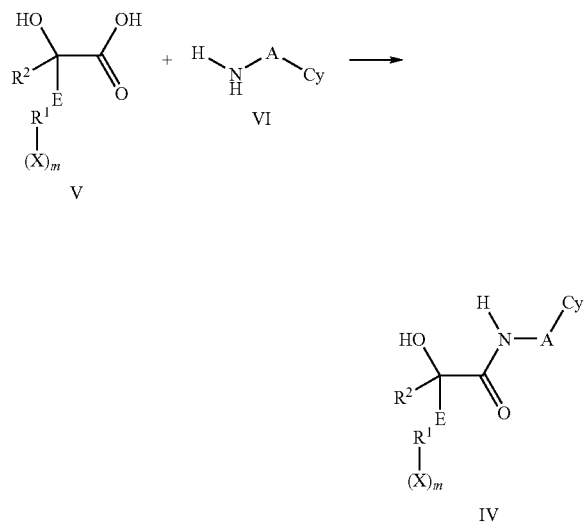

Certain α-hydroxyacids of Formula V are commercially available. α-Hydroxyacids of Formula V can be prepared by diazotization of α-amino acids of Formula VII using $NaNO_2$ in $H_2SO_4$:

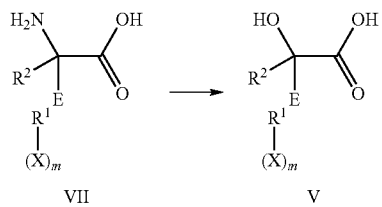

α-Hydroxyacids of Formula V can also be prepared from ketones Formula VIII via cyanohydrins of Formula IX:

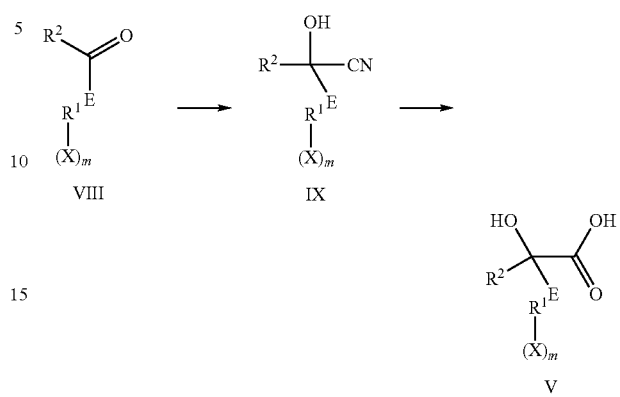

Methods for the conversion of ketones to cyanohydrins are described in Smith, M. B. and March, J. "March's Advanced Organic Chemistry" pp 1239-1240, 5th Edition, Wiley, New York, N.Y., 2001. Methods for the hydrolysis of cyanohydrins to α-hydroxyacids are described in Smith, M. B. and March, J. "March's Advanced Organic Chemistry" p 1179, 5th Edition, Wiley, New York, N.Y., 2001

α-hydroxyacids of Formula V, wherein $R^1$ is not H when E is a bond and $R^2$ is not H, can also be prepared by oxidation of diols of Formula X with for example oxygen in the presence of a catalyst or using sodium chlorite and TEMPO:

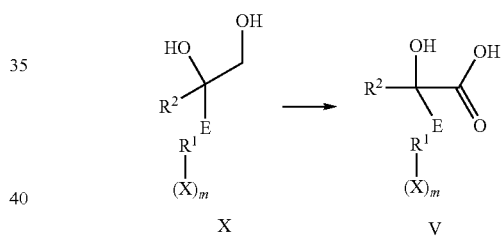

Amine intermediates of Formula VI wherein A is $CH_2$ can be prepared by reduction of amides of Formula XI using a hydride reagent such as $BH_3.THF$ solution, $BH_3.Me_2S$ or $LiAlH_4$ in an inert solvent ethereal such as THF or DME at 20° C. to 100° C. for between 1 h and 48 h:

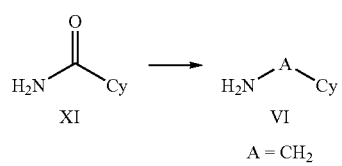

$A = CH_2$

Amine intermediates of Formula VI wherein A is a bond can be prepared from ketones of formula XII via oximes of Formula XIII:

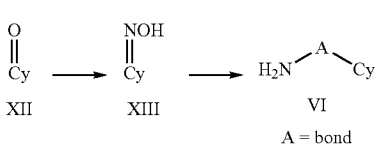

$A = bond$

Methods for the conversion of ketones to oximes are described in Smith, M. B. and March, J. "March's Advanced Organic Chemistry" pp 1194-1195, 5th Edition, Wiley, New York, N.Y., 2001. Methods for the reduction of oximes to primary amines are described in Smith, M. B. and March, J. "March's Advanced Organic Chemistry" p 1555, 5th Edition, Wiley, New York, N.Y., 2001.

Intermediates of Formula II wherein Q is O, G is $CH_2$ and n is 0 can be prepared by reaction of epoxides of Formula XIV with amines of Formula VI as described in Smith, M. B. and March, J. "March's Advanced Organic Chemistry" p 504, 5th Edition, Wiley, New York, N.Y., 2001:

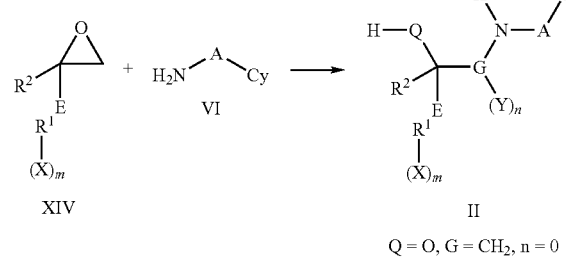

Q = O, G = $CH_2$, n = 0

Epoxide compounds of formula XIV can, in turn, be prepared in a number of ways including, as described in Aube, J. "Epoxidation and Related Processes" Chapter 3.2 in Volume 1 of "Comprehensive Organic Synthesis" Edited by B. M. Trost, I. Fleming and Stuart L. Schreiber, Pergamon Press, New York, 1992).

Analogously intermediates of Formula II wherein G is $CH_2CH_2$ can be prepared by reaction of oxetanes of Formula XV with amines of Formula VI as described in Smith, M. B. and March, J. "March's Advanced Organic Chemistry" p 505, 5th Edition, Wiley, New York, N.Y., 2001:

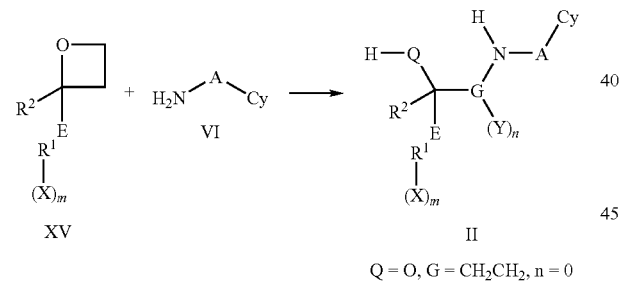

Q = O, G = $CH_2CH_2$, n = 0

Intermediates of Formula II wherein A is $CH_2$ can be prepared by reduction of amide intermediates of formula XVI using a hydride reagent such as $BH_3$.THF solution, $BH_3.Me_2S$ or $LiAlH_4$ in an inert solvent ethereal such as THF or DME at 20° C. to 100° C. for between 1 h and 48 h:

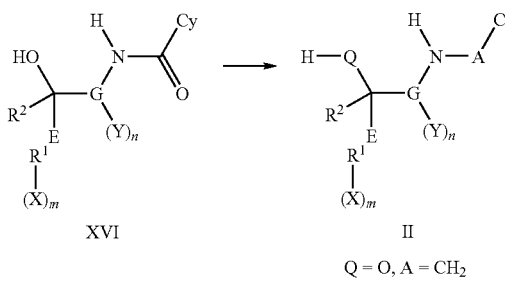

Q = O, A = $CH_2$

Amide intermediates of Formula XVI can be prepared by reaction of an amino-alcohol intermediate of Formula XVII with activated carboxylic acid of Formula XVIII wherein $Z^3$ is chloride or an activated ester, such as an N-hydroxysuccinimide ester:

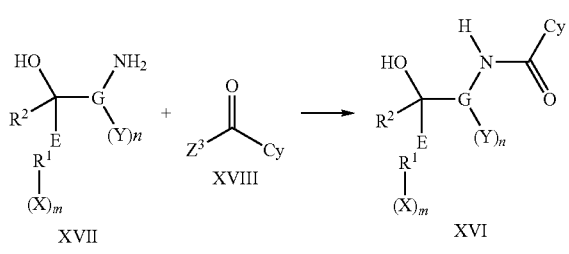

Amino-alcohol intermediates of Formula XVII wherein G is $CH_2$ and n is 0 can be prepared by reaction of an epoxide of Formula XIV with azide ion to give an azido-alcohol of Formula XIX followed by reduction of the azide moiety with hydrogen gas or using triphenylphosphine in the presence of water:

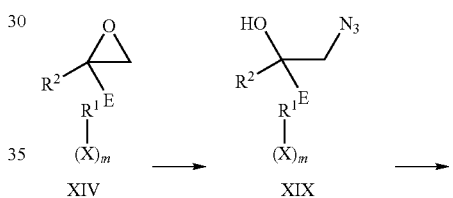

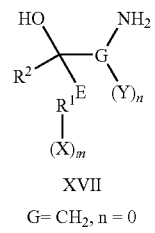

G = $CH_2$, n = 0

Amino-alcohol intermediates of Formula XVII wherein G is $CH_2CH_2$ and n is 0 can be prepared by reaction of an epoxide of Formula XIV with cyanide ion followed by reduction of the resulting hydroxynitrile of Formula XX with hydrogen gas in the presence of a catalyst or with a hydride source such as $LiAlH_4$:

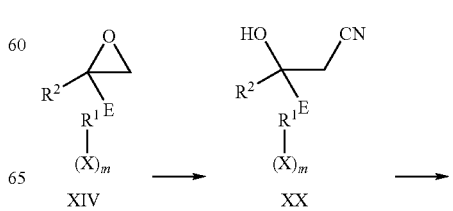

-continued

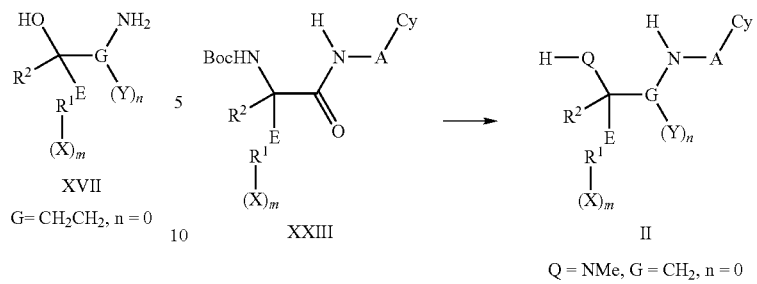

Intermediates of Formula II wherein Q is N, R³ is H, G is CH₂ and n is 0 can be prepared by reduction of α-aminoamides of Formula XXI using a hydride reagent such as BH₃.THF solution, BH₃.Me₂S or LiAlH₄ in an inert solvent ethereal such as THF or DME at 20° C. to 100° C. for between 1 h and 48 h:

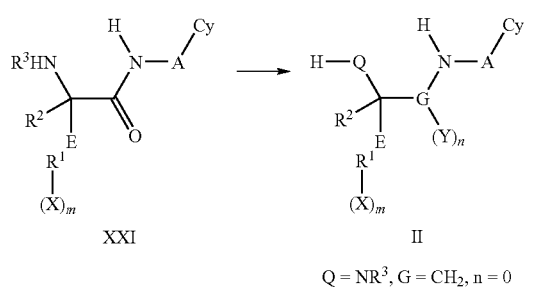

α-Aminoamides of Formula XXI can be prepared by coupling of a suitably N-protected α-amino-acid of Formula XXII with an amine of Formula VI using standard peptide coupling reagents such as EDC with HOBt or HATU in the presence of N,N-diisopropylethylamine in an inert solvent such as CH₂Cl₂ at 0-30° C. for between 1 h and 24 h followed by removal of the protecting group:

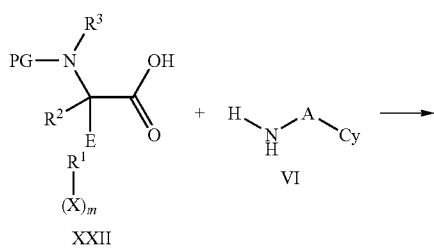

PG = protecting group

Intermediates of Formula II wherein Q is N, R³ is Me, G is CH₂ and n is 0 can be prepared by reduction of α-(tert-butoxycarbonylamino)amides of Formula XXIII using LiAlH₄ in an inert solvent ethereal such as THF or DME at reflux for between 6 h and 72 h:

Intermediates of Formula II wherein Q is N, R³ is H, G is CH₂CH₂ and n is 0 can be prepared by reduction of β-aminoamides of Formula XXIV using a hydride reagent such as BH₃.THF solution, BH₃.Me₂S or LiAlH₄ in an inert solvent ethereal such as THF or DME at 20° C. to 100° C. for between 1 h and 48 h:

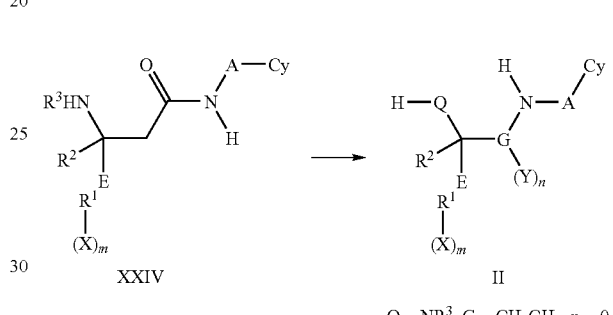

Intermediates of Formula II can be prepared by ring opening of aziridines of Formula XXV wherein PG is a protecting group such as Boc or Ts with amines of Formula VI followed by removal of PG:

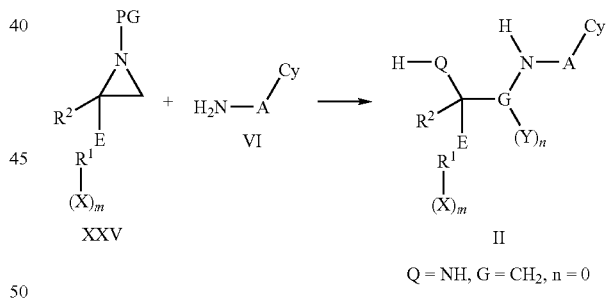

Intermediates of Formula II wherein G is CH₂ and n is 0 can also be prepared by reductive amination of aldehyde intermediates of Formula XXVI with amines of Formula VI using for example NaCNBH₃ or NaBH(OAc)₃ as reducing agent:

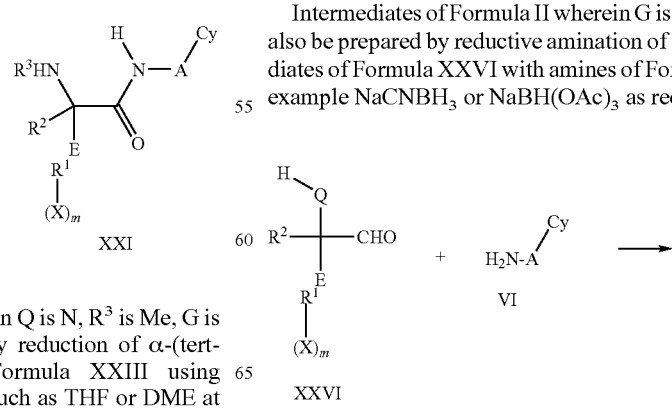

-continued

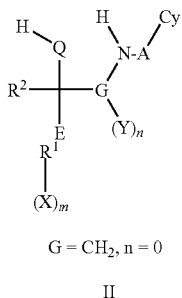

G = CH$_2$, n = 0

II

Additional methods for the synthesis of 1,2-diamine intermediates of Formula II wherein Q=NR$^3$ are described in Lucet, D.; Le Gall, T.; Mioskowski, C. *Angew. Chem. Int. Ed.* 1998, 37, 2580-2617.

In the second process a compound of Formula I wherein Q is O can be prepared by reaction of a carbamate intermediate of Formula XXVII wherein R$^a$ is alkyl or benzyl with an epoxide intermediate of Formula XIV in the presence of a strong base such as NaH in a solvent such as THF or DMF at 0° C. to 80° C.:

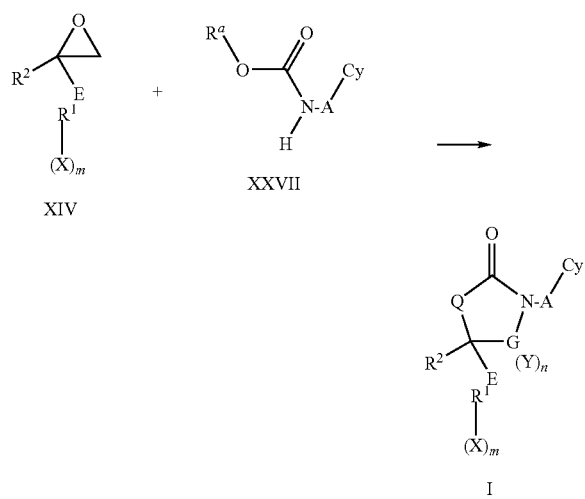

Carbamate intermediates of Formula XXVII can be prepared by reaction of amines of Formula VI with chloroformates of Formula XXVIII in the presence of a base such as pyridine or triethylamine in an inert solvent such as CH$_2$Cl$_2$ or THF at 0° C. to 25° C. for between 1 h and 24 h:

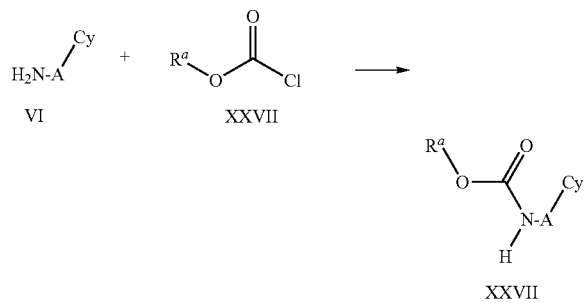

In the third process of the invention a compound of Formula I can be prepared from another compound of Formula I. For example:

(1) a compound of Formula I wherein Cy bears a CO$_2$H substituent can be converted to the corresponding acid chloride by treatment with SOCl$_2$ or (COCl)$_2$ and then reacted with ammonia to give a compound of Formula I wherein Cy bears a CONH$_2$ substituent.

(2) a compound of Formula I wherein Cy bears a CONH$_2$ substituent can be treated with a dehydrating agent such as (CF$_3$CO)$_2$O or POCl$_3$ to convert it to a compound of Formula I wherein Cy bears a CN substituent.

(3) a compound of Formula I wherein Cy bears a CO$_2$Me substituent can be reduced with for example LiBH$_4$ or LiAlH$_4$ in THF to give a compound of Formula I wherein Cy bears a CH$_2$OH substituent.

(4) a compound of Formula I wherein Cy bears a CO$_2$Me substituent can be reacted with an excess of MeLi or MeMgBr to give a compound of Formula I wherein Cy bears a C(CH$_3$)$_2$OH substituent.

(5) a compound of Formula I wherein Q is NR$^3$ and R$^3$ is H can be reacted with a strong base such as NaH followed by an (C$_1$-C$_8$)alkyl halide, a (C$_1$-C$_4$)alkoxy(C$_1$-C$_4$)alkyl halide or a phenyl(C$_1$-C$_4$)alkyl halide to give a compound of Formula I wherein Q is NR$^3$ and R$^3$ is (C$_1$-C$_8$)alkyl, (C$_1$-C$_4$)alkoxy(C$_1$-C$_4$)alkyl or phenyl(C$_1$-C$_4$)alkyl.

(6) a compound of Formula I wherein R$^1$ is aryl or heteroaryl and X is bromine or iodine can be reacted with an aryl or heteroarylboronic acid or ester in the presence of a palladium catalyst to give a compound of Formula I wherein R$^1$ is aryl or heteroaryl and X is aryl or heteroaryl.

Purification Methods

Compounds of the invention may be purified by high pressure liquid chromatography (HPLC) using the following conditions. Unless otherwise specified, prep HPLC refers to preparative reverse phase HPLC on a C-18 column eluted with a water/acetonitrile gradient containing 0.01% TFA run on a Gilson 215 system.

Analytical Methods

LC-MS (3 min)
Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
| --- | --- | --- |
| 0.0 | 90 | 10 |
| 2.0 | 10 | 90 |
| 2.4 | 10 | 90 |
| 2.5 | 90 | 10 |
| 3.0 | 90 | 10 |

LC-MS (4 min)
Column: YMC ODS-AQ, S-5 mm, 12 nm, 50×2.0 mm ID; Column temperature 40° C.; Mobil phase: A: H2O+0.1% TFA, B: MeCN+0.05% TFA; Flow rate: 0.8 mL/min; Gradient:

| Time (min) | A % | B % |
| --- | --- | --- |
| 0.00 | 100 | 0 |
| 0.4 | 100 | 0 |

-continued

| Time (min) | A % | B % |
|---|---|---|
| 2.00 | 40 | 60 |
| 2.50 | 40 | 60 |
| 2.51 | 100 | 0 |
| 4.00 | 100 | 0 |

LC-MS (16 min)
Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 14.0 | 10 | 90 |
| 15.0 | 10 | 90 |
| 15.1 | 90 | 10 |
| 16.0 | 90 | 10 |

EXAMPLES

Example 1

(S)-3-((1-adamantyl)methyl)-5-phenyloxazolidin-2-one

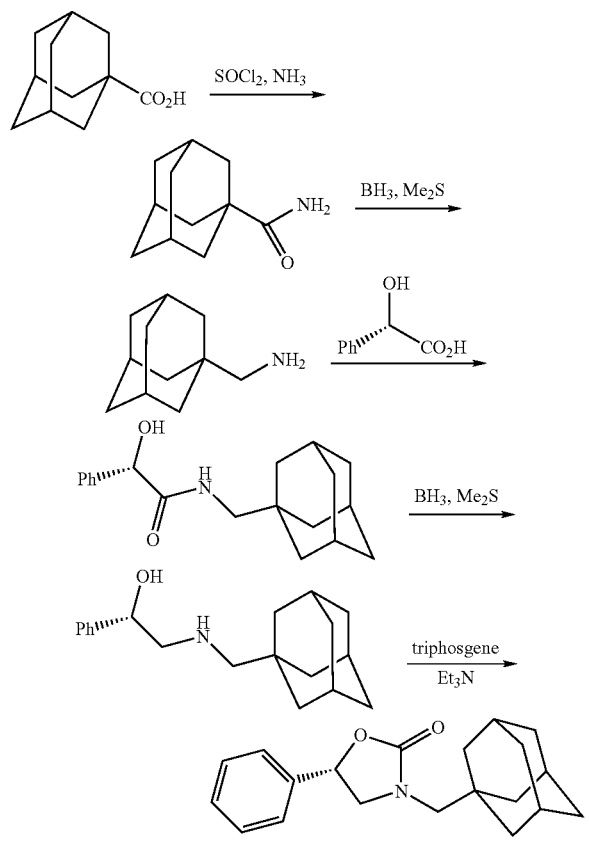

Step 1
Adamantane-1-carboxylic acid (10 g, 55 mmol) was heated at reflux with thionyl chloride (15 mL) and dimethylformamide (1 drop) for 2 h under an inert atmosphere. Excess thionyl chloride was distilled off under vacuum. The residue was dissolved in THF (30 mL) and added to a solution of concentrated aqueous ammonia (135 mL) at 0° C. The reaction was stirred for 2 h at rt. The mixture was cooled to 10° C. and filtered to give the crude product, which was washed with water and dried to afford admantane-1-carboxamide (6.6 g, 67%). $^1$H NMR (CDCl$_3$, 400 MH$_z$): δ=1.71-2.04 (t, 15H), 5.66-5.75 (d, 2H).

Step 2
To a solution of admantane-1-carboxamide (2 g, 11.17 mmol) in THF (50 mL) was added BH$_3$.Me$_2$S (10.2 M, 3.4 mL, 34.7 mmol) under nitrogen. The mixture was heated at reflux overnight. The solution was cooled to rt. Methanol (20 mL) was added to the solution. The mixture was concentrated under vacuum to give crude product, which was purified by chromatography on silica gel to afford (1-adamantyl)methylamine (1.09 g, 59%). $^1$H NMR (CDCl$_3$, 400 MHz): δ=1.44-1.96 (m, 15H), 2.30 (s, 2H).

Step 3
To a solution of (1-adamantyl)methylamine (100 mg, 0.61 mmol), (S)-2-hydroxy-2-phenylacetic acid (92 mg, 0.61 mmol), EDCI (239 mg, 1.22 mmol) and HOBt (164 mg, 1.22 mmol) in CH$_2$Cl$_2$ (15 mL) was added DIEA (391 mg, 3.03 mmol) and the resulting mixture was stirred overnight. The solution was concentrated under vacuum to give the crude product, which was purified by preparative TLC to afford (S)—N-((1-adamantyl)methyl)-2-hydroxy-2-phenylacetamide (85 mg, 47%). $^1$H NMR (CDCl$_3$, 400 MHz): δ=1.34-1.91 (m, 15H), 2.86 (q, 1H), 3.02 (q, 1H), 5.04 (s, 1H), 5.93 (s, 1H), 7.25-7.43 (m, 5H).

Step 4
To a solution of (S)—N-((1-adamantyl)methyl)-2-hydroxy-2-phenylacetamide (85 mg, 0.28 mmol) in THF (10 mL) was added BH$_3$.Me$_2$S (10 M, 85 μL, 8.5 mmol) under nitrogen. The mixture was heated under reflux overnight and then cooled to rt. The reaction was quenched with methanol. The mixture was concentrated in vacuum to give crude product, which was purified by preparative TLC to afford (S)-2-((1-adamantylmethyl)amino)-1-phenylethanol (40 mg, 50%). $^1$H NMR (MeOD, 400 MH$_z$): δ=1.31-2.01 (m, 15H), 2.42 (q, 2H), 2.81 (d, 2H), 4.88 (t, 1H), 7.21-7.43(m, 5H).

Step 5
To a solution of (S)-2-((1-adamantylmethyl)amino)-1-phenylethanol (35 mg, 0.12 mmol), Et$_3$N (24.8 mg, 0.25 mmol) in CH$_2$Cl$_2$ (2 mL) at 0° C. was added triphosgene (14.6 mg, 0.05 mmol) and the mixture was stirred for 30 min. The mixture was concentrated under vacuum to give the crude product, which was purified by preparative TLC to give (S)-3-((1-adamantyl)methyl)-5-phenyloxazolidin-2-one (10 mg, 26%). $^1$H NMR (MeOD, 400 MH$_z$): δ=1.51-1.95 (m, 15H), 2.89 (q, 2H), 3.55 (q, 1H), 4.10 (t, 1H), 5.57 (q, 1H), 7.34~7.45 (m, 5H); MS m/z=312.

Example 2

(S)-3-((1-adamantyl)methyl)-5-isobutyloxazolidin-2-one

The title compound was prepared following procedures analogous to those described in Example 1 using (S)-2-hydroxy-4-methylpentanoic acid in Step 3. $^1$H NMR (MeOD, 400 MH$_z$): δ 0.97 (d, 6H), 1.40-1.97 (m, 18H), 2.81 (dd, 2H), 3.78 (t, 1H), 4.63 (m, 1H); MS m/z=292

Example 3

(R)-3-((1-adamantyl)methyl)-5-phenyloxazolidin-2-one

The title compound was prepared following procedures analogous to those described in Example 1 Steps 3-5 using (R)-2-hydroxy-2-phenylacetic acid in Step 3. $^1$H NMR (MeOD, 400 MH$_z$): δ 1.62 (m, 6H), 1.64-1.96 (m, 6H), 2.05 (m, 3H), 3.01 (m, 2H), 3.65 (m, 1H), 4.19 (m, 1H), 5.66 (m, 1H), 7.49 (m, 5H); MS m/z=312.

Example 4

(S)-3-(1-adamantyl)-5-isobutyloxazolidin-2-one

The title compound was prepared following procedures analogous to those described in Example 1 Steps 3-5 using (S)-2-hydroxy-4-methylpentanoic acid and 1-aminoadamantane in Step 3. $^1$H NMR (MeOD, 400 MH$_z$): δ 0.99(d, 6H), 1.46(m, 1H), 1.59-1.90(m, 9H), 2.11(m, 9H), 3.25(m, 1H), 3.78(t, 1H), 4.49(m, 1H); MS m/z=278

Example 5

(S)-3-(2-adamantyl)-5-isobutyloxazolidin-2-one

The title compound was prepared following procedures analogous to those described in Example 1 Steps 3-5 using (S)-2-hydroxy-4-methylpentanoic acid and 2-aminoadamantane hydrochloride in Step 3. $^1$H NMR (MeOD, 400 MH$_z$): δ 0.98(d, 6H), 1.49(m, 1H), 1.61-2.02(m, 14H), 2.28(m, 1H), 2.40(m, 1H), 3.36(m, 1H), 3.65(m, 1H), 3.90(t, 1H), 4.61(m, 1H); MS m/z=278

Example 6

(S)-5-benzyl-3-((1-adamantyl)methyl)oxazolidin-2-one

The title compound was prepared following procedures analogous to those described in Example 1 using (S)-2-hydroxy-3-phenylpropanoic acid in Step 3. $^1$H NMR (MeOD, 400 MHz): δ 1.39(m, 6H), 1.64(m, 6H), 1.90(m, 3H), 2.72 (dd, 2H), 3.00(m, 2H), 3.42(m, 1H), 3.67(t, 1H), 4.75(m, 1H), 7.29(m, 5H); MS m/z=326

Example 7

(S)-3-((1-adamantyl)methyl)-5-(2-chlorophenyl)oxazolidin-2-one

The title compound was prepared following procedures analogous to those described in Example 1 using (S)-2-(2-chlorophenyl)-2-hydroxyacetic acid in Step 3. $^1$H NMR (MeOD, 400 MH$_z$): δ 1.50(m, 6H), 1.62(m, 6H), 1.92(m, 3H), 2.90(m, 2H), 3.51(m, 1H), 4.23(m, 1H), 5.84(m, 1H), 7.46(m, 4H); MS m/z=346

Example 8

(S)-3-((1-adamantyl)methyl)-5-(t-butyl)oxazolidin-2-one

The title compound was prepared following procedures analogous to those described in Example 1 using (S)-2-hydroxy-3,3-dimethylbutanoic acid in Step 3. $^1$H NMR (MeOD, 400 MH$_z$): δ 0.95 (s, 9H), 1.58 (m, 6H), 1.72 (m, 6H), 1.99 (m, 3H), 2.88 (dd, 2H), 3.48 (m, 1H), 3.66 (m, 1H), 4.28 (m, 1H); MS m/z=292

Example 9

(±)-3-((1-adamantyl)methyl)-5-(3-chlorophenyl)oxazolidin-2-one

The title compound was prepared following procedures analogous to those described in Example 1 using 2-(3-chlorophenyl)-2-hydroxyacetic acid in Step 3. $^1$H NMR (MeOD, 400 MH$_z$): δ 1.48-1.85 (m, 12H), 1.95 (m, 3H), 2.90 (m, 2H), 3.52 (m, 1H), 4.11 (m, 1H), 5.56 (m, 1H), 7.29-7.48 (m, 4H); MS m/z=346.

Example 10

(S)-3-((1-adamantyl)methyl)-5-ethyloxazolidin-2-one

The title compound was prepared following procedures analogous to those described in Example 1 using (S)-2-hydroxybutanoic acid in Step 3. $^1$H NMR (MeOD, 400 MH$_z$): δ 1.00(t, 3H), 1.52(m, 6H), 1.56-1.72(m, 8H), 1.98(m, 3H), 2.86(dd, 2H), 3.25(m, 1H), 3.69(m, 1H), 4.42(m, 1H); MS m/z=264.

Example 11

(S)-3-((2-adamantyl)methyl)-5-phenyloxazolidin-2-one

The title compound was prepared following procedures analogous to those described in Example 1 Steps 3-5 using (2-adamantylmethyl)amine in Step 3. $^1$H NMR (MeOD, 400 MHz): δ 1.5(m, 2H), 1.72(m, 6H), 1.82-2.00(m, 7H), 3.38(m, 2H), 3.51(m, 1H), 3.90(t, 1H), 5.48(t, 1H), 7.36-7.44(m, 5H); MS m/z=312.

Example 12

(S)-3-(2-adamantyl)-5-tert-butyloxazolidin-2-one

The title compound was prepared following procedures analogous to those described in Example 1 Steps 3-5 using (S)-2-hydroxy-3,3-dimethylbutanoic acid and 2-aminoadamantane hydrochloride in Step 3. $^1$H NMR (CDCl$_3$) 0.94 (s, 9H), 1.60-2.0 (12H), 2.26 (br s, 1H), 2.42 (br s, 1H), 3.43 (t, 1H), 3.62 (t, 1H), 3.69 (br s, 1H), 4.14 (t, 1H); LC-MS (3 min) t$_R$=2.09 min, m/z=278.

Example 13

(S)-3-(1-hydroxy-4-adamantyl)-5-isobutyloxazolidin-2-one

The title compound was prepared following procedures analogous to those described in Example 1 Steps 3-5 using (S)-2-hydroxy-4-methylpentanoic acid and 1-hydroxy-4-aminoadamantane in Step 3. The isomers were separated by preparative HPLC to afford (S)-3-(1-hydroxy-4-adamantyl)-5-isobutyloxazolidin-2-one Isomer A and (S)-3-(1-hydroxy-4-adamantyl)-5-isobutyloxazolidin-2-one Isomer B. Isomer A: $^1$H NMR (MeOD, 400 MHz): δ 0.98(d, 6H), 1.52(m, 3H), 1.76(m, 8H), 1.86(m, 3H), 2.14(m, 1H), 2.46(m, 1H), 2.64(m, 1H), 3.56(m, 1H), 3.87(t, 1H), 4.60(m, 1H).; MS m/z=294.

Isomer B: $^1$H NMR (MeOD, 400 MH$_Z$): δ 0.98(d, 6H), 1.48 (m, 3H), 1.60(m, 2H), 1.74(m, 7H), 1.88(m, 3H), 2.10(m, 1H), 2.56(m, 1H), 2.65(m, 1H), 3.47(m, 1H), 3.86(t, 1H), 4.60(m, 1H), MS m/z=294.

Example 14

(S)-3-(2-adamantyl)-5-phenyloxazolidin-2-one

The title compound was prepared following procedures analogous to those described in Example 1 Steps 3-5 using (S)-2-hydroxy-2-phenylacetic acid and 2-aminoadamantane hydrochloride in Step 3. $^1$H NMR (MeOD, 400 MH$_Z$): δ 1.55(m, 6H), 1.67(d, 2H), 1.75(m, 2H), 1.91(m, 8H), 2.28(m, 1H), 2.49(m, 1H), 3.58(m, 1H), 3.74(m, 1H), 4.09(m, 1H), 5.49(m, 1H), 7.40(m, 5H); MS m/z=298.

Example 15

(R)-3-(2-adamantyl)-5-phenyloxazolidin-2-one

The title compound was prepared following procedures analogous to those described in Example 1 Steps 3-5 using (R)-2-hydroxy-2-phenylacetic acid and 2-aminoadamantane hydrochloride in Step 3. $^1$H NMR (MeOD, 400 MH$_Z$): δ 1.56(m, 3H), 1.66(d, 2H), 1.86(m, 8H), 2.28(m, 1H), 2.48(m, 1H), 3.54(t, 1H), 3.75(m, 1H), 4.07(m, 1H), 5.48(t, 1H), 7.400(m, 5H); MS m/z=298

Example 16

(S)-3-(2-adamantyl)-5-methyl-5-phenyloxazolidin-2-one

The title compound was prepared following procedures analogous to those described in Example 1 Steps 3-5 using (S)-2-hydroxy-2-phenylpropanoic acid and 2-aminoadamantane hydrochloride in Step 3. $^1$H NMR (CDCl$_3$) 1.50-1.90 (15H), 2.26 (br s, 1H), 2.43 (br s, 1H), 3.72 (s, 1H), 3.79 (m, 2H), 7.25-7.45 (5H); LC-MS (3 min) t$_R$=2.11 min, m/z=286.

Example 17

3-(1-adamantylmethyl)-5-(4-hydroxyphenyl)oxazolidin-2-one

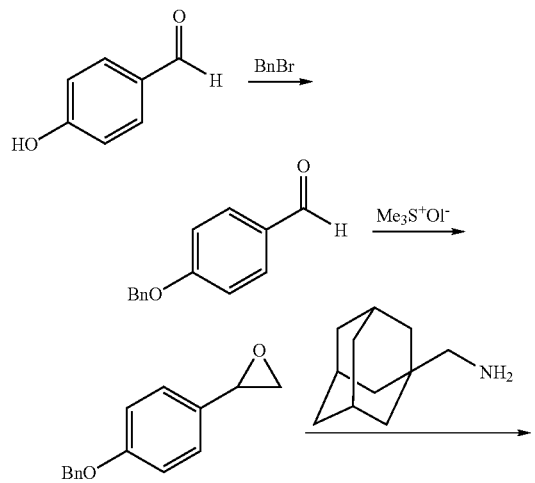

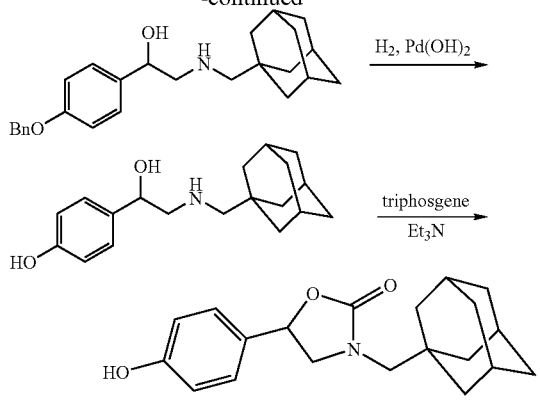

Step 1

To a stirred mixture of 4-hydroxybenzaldehyde (28.2 g, 231 mmol), potassium carbonate (47.9 g, 35 mmol), potassium iodide and DMF(280 mL) benzyl bromide was added slowly at 0° C. The mixture was stirred at rt overnight. The mixture was diluted with EtOAc and water. The layers were separated and the aqueous layer was extracted with EtOAc. The combined organic layers were washed with 1N aq HCl and dried. The solution was concentrated to give 4-benzyloxybenzaldehyde (46.5 g, 95%). $^1$H NMR: (CDCl$_3$, 400 MH$_Z$) δ=5.15 (s, 2H), 7.06 (m, 2H), 7.42(m, 5H), 7.84(m, 2H), 9.89(s, 1H).

Step 2

NaH (60%, 0.5 g, 23.6 mmol) was diluted in DMSO (50 mL) and stirred for 30 min at rt under nitrogen. Trimethylsulfoxonium iodide (7.8 g, 35.37 mmol) was added in portions at 0° C. The reaction mixture was stirred for 1 h. Then a solution of 4-benzyloxybenzaldehyde (5 g, 23.58 mmol) in THF (15 mL) was added. The reaction solution was stirred at rt for 3 h. The reaction mixture was poured into ice-water and extracted with ether. The organic layer was dried over Na$_2$SO$_4$ and concentrated to give 2-(4-(benzyloxy)phenyl) oxirane, which was used for the next step without further purification.

Step 3

2-(4-(benzyloxy)phenyl)oxirane (2 g, 8.8 mmol) and (1-adamantylmethyl)amine (1.46 g, 8.8 mol) were dissolved in isopropyl alcohol (30 mL) and heated under reflux overnight. The mixture was concentrated to give the crude product, which was purified by column chromatography to afford 1-(4-(benzyloxy)phenyl)-2-((1-adamantylmethyl)amino) ethanol (0.8 g, 23%). $^1$H NMR: (CDCl$_3$, 400 MHz) δ=1.51 (m, 6H), 1.60-1.72 (m, 6H), 1.97 (m, 3H), 2.32&2.45 (dd, 2H), 2.64 (m, 1H), 2.73 (m, 1H), 2.94 (m, 1H), 3.40 (brs, 3H), 4.79 (m, 1H), 6.93 (m, 2H), 7.26-7.43 (m, 7H).

Step 4

To a solution of 1-(4-(benzyloxy)phenyl)-2-((1-adamantylmethyl)amino)ethanol (0.8 g, 2.05 mmol) in MeOH (10 mL) was added Pd(OH)$_2$ (80 mg). The mixture was stirred at rt under H$_2$ for 30 min. The mixture was filtered and concentrated to give 4-(2-((1-adamantylmethyl)amino)-1-hydroxyethyl)phenol (0.5 g, yield: 81%). $^1$H NMR: (CDCl$_3$, 400 MHz) δ=1.53 (m, 6H), 1.65 (m, 6H), 1.97 (m, 3H), 2.26 & 2.36 (dd, 2H), 2.62&2.83 (dd, 2H), 4.60 (m, 1H), 6.78 (m, 2H), 7.22 (m, 2H).

Step 5

4-(2-((1-adamantylmethyl)amino)-1-hydroxyethyl)phenol (50 mg, 0.166 mmol) and Et$_3$N (34 mg, 0.33 mmol) were dissolved in dry CH$_2$Cl$_2$ (1 mL) and the solution was cooled to 0° C. Triphosgene (19.7 mg, 0.066 mmol) in dry CH$_2$Cl$_2$ (1 mL) was added dropwise slowly. The mixture was allowed to warm to rt and stirred overnight. The solution was concentrated to give a residue, which was purified by preparative HPLC to afford 3-adamantan-1-ylmethyl-5-(4-hydroxy-phenyl)-oxazolidin-2-one (2.40 mg, 4.4%). $^1$H NMR: (CDCl$_3$, 400 MHz): δ=1.54 (s, 6H), 1.58-1.65 (d, 3H), 1.66-1.75 (d, 3H), 1.99 (s, 3H), 2.80-2.87 (d, 1H), 3.02-3.08 (d, 1H), 3.50-3.56 (t, 1H), 3.93-4.00 (t, 1H), 5.40-5.48 (t, 1H), 6.82-6.90 (d, 1H), 7.20-7.26 (d, 1H); MS m/z=328

Example 18

(S)-3-((1-adamantyl)methyl)-5-cyclohexyloxazolidin-2-one

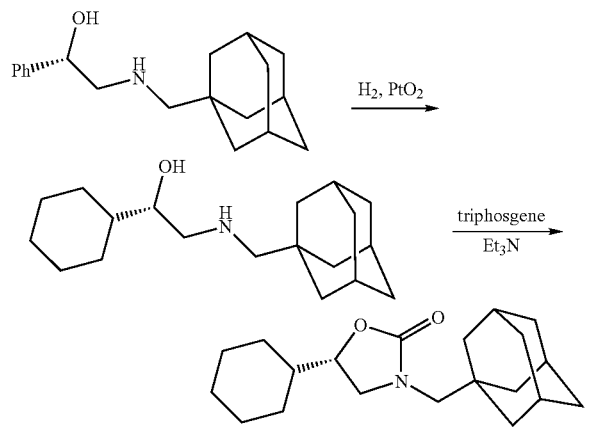

Step 1

To a solution of (S)-2-((1-adamantylmethyl)amino)-1-phenylethanol (50 mg, 0.18 mmol) in dry CH$_3$OH (5 mL) was added PtO$_2$ (10 mg) as the catalyst. The mixture was stirred under hydrogen (55 psi) at 60-70° C. overnight. After filtration, the filtrate was evaporated to give a residue, which was purified by preparative TLC to give (S)-1-cyclohexyl-2-((1-adamantylmethyl)amino)ethanol (20 mg, 40%). $^1$H NMR (MeOD, 400 MHz): δ=1.07-1.99 (m, 25H), 2.35-2.51 (q, 2H), 2.63 (t, 1H), 2.80 (d, 1H), 3.51 (m, 1H).

Step 2

To a solution of (S)-1-cyclohexyl-2-((1-adamantylmethyl)amino)ethanol (22 mg, 0.077 mmol) and Et$_3$N (15.6 mg, 0.154 mmol) in dry CH$_2$Cl$_2$(2 mL) at 0° C. was added triphosgene (9.2 mg, 0.031 mmol) in dry CH$_2$Cl$_2$(2 mL). The mixture was stirred for 30 min and then concentrated in vacuum to give the crude product, which was purified by preparative TLC to afford (S)-3-((1-adamantyl)methyl)-5-cyclohexyloxazolidin-2-one (5 mg, 21%). $^1$H NMR (MeOD, 400 MHz): δ=1.18-1.97 (m, 25H), 2.75-2.95 (m, 2H), 3.42 (t, 1H), 3.72 (t, 1H), 4.83 (m, 1H); MS: m/z=318.

Example 19

(S)-3-((2-adamantyl)methyl)-5-cyclohexyloxazolidin-2-one

The title compound was prepared following procedures analogous to those described in Example 18 using (S)-2-((2-adamantylmethyl)amino)-1-phenylethanol in Step 1. $^1$H NMR (MeOD, 400 MHz): δ 1.04(m, 2H), 1.22(m, 3H), 1.56 (m, 8H), 1.72(m, 7H), 1.80-2.00(m, 6H), 3.25(m, 2H), 3.47 (m, 2H), 4.20(m, 1H).; MS m/z=318.

Example 20

(S)-3-(2-adamantyl)-5-cyclohexyloxazolidin-2-one

The title compound was prepared following procedures analogous to those described in Example 18 using (S)-2-(2-adamantylamino)-1-phenylethanol in Step 1. $^1$H NMR (MeOD, 400 MHz): δ 0.96-1.18 (m, 3H), 1.19-1.36 (m, 3H), 1.48-1.62 (m, 9H), 1.76 (m, 4H), 1.77-1.99 (m, 9H), 2.23(m, 1H), 2.44(m, 1H), 3.38 (t, 1H), 3.70(m, 2H), 4.18(m, 1H); MS m/z=304.

Example 21

(R)-3-(2-adamantyl)-5-cyclohexyloxazolidin-2-one

The title compound was prepared following procedures analogous to those described in Example 18 using (R)-2-(2-adamantylamino)-1-phenylethanol in Step 1. $^1$H NMR (MeOD, 400 MHz): δ 0.97-1.16(m, 3H), 1.18-1.36(m, 4H), 1.49-1.72(m, 11H), 1.75(m, 5H), 1.77-2.01(m, 9H), 2.23(m, 1H), 2.44(m, 1H), 3.39(t, 1H), 3.60(m, 2H), 4.17(m, 1H); MS m/z=304.

Example 22

3-(1-adamantylmethyl)-5-(4-hydroxycyclohexyl)oxazolidin-2-one

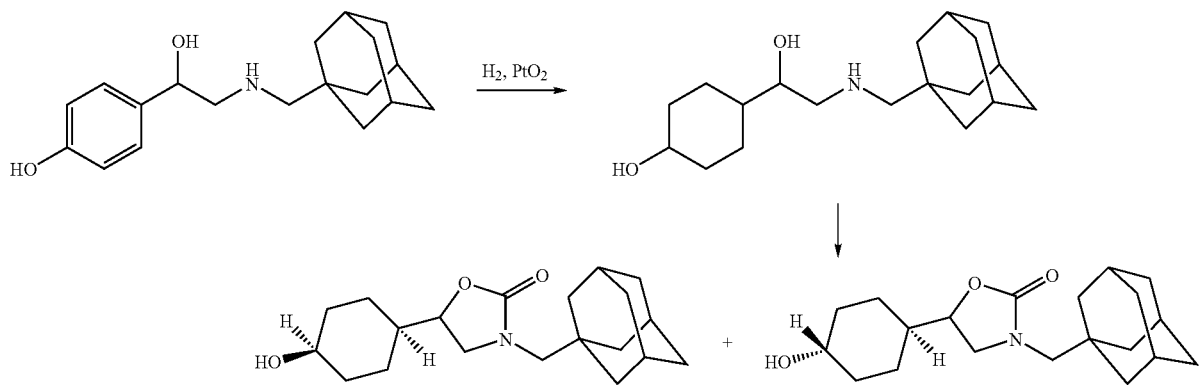

Step 1

To a solution of 4-(2-((1-adamantylmethyl)amino)-1-hydroxyethyl)phenol (0.3 g, 1 mmol) in MeOH (10 mL) was added PtO$_2$ (60 mg). The mixture was stirred under hydrogen (50 psi) at 60° C. for 2 d. The solvent was removed and purified by preparative TLC to give 4-(2-(1-adamantylmethylamino)-1-hydroxyethyl)cyclohexanol (100 mg, 32%). $^1$H NMR: (400 MH$_Z$, CDCl$_3$) δ=0.90-1.40 (m, 5H), 1.46 (m, 6H), 1.50-1.65 (m, 6H), 1.66-1.82 (m, 2H), 1.92 (m, 3H), 2.25 (m, 2H), 3.30 (m, 5H), 4.41 (m, 1H).

Step 2

To a solution of 4-(2-(1-adamantylmethylamino)-1-hydroxyethyl)cyclohexanol (180 mg, 0.58 mmol) and triethylamine (117 mg, 1.16 mmol) in CH$_2$Cl$_2$ (2 mL), was added triphosgene (70 mg, 0.23 mmol). The mixture was stirred at rt overnight. The solvent was removed and the residue was purified by preparative TLC to give crude 3-(2-adamantyl)-5-(4-hydroxycyclohexyl)oxazolidin-2-one, which was separated by MS-trigger HPLC to afford isomer A (9.57 mg) and isomer B (2.27 mg).

Isomer A $^1$H NMR: (400 MH$_Z$, CDCl$_3$) δ=1.14-1.31 (m, 4H), 1.56 (m, 11H), 1.63&1.73 (m, 4H), 2.05 (m, 4H), 2.74&2.99 (dd, 2H), 3.32 (m, 1H), 3.62 (m, 2H), 4.23 (m, 1H); MS m/z=334.

Isomer B $^1$H NMR: (400 MH$_Z$, CDCl$_3$) δ=1.31-1.50 (m, 3H), 1.50 (m, 6H), 1.62&1.71 (m, 6H), 1.82 (m, 2H), 2.00 (m, 3H), 2.16 (m, 6H), 2.72&3.03 (dd, 2H), 3.35 (m, 1H), 3.64 (m, 1H), 4.08 (m, 1H), 4.30 (m, 1H); MS m/z=334.

Example 23

3((1-adamantyl)methyl)-6-isobutyl-1,3-oxazinan-2-one

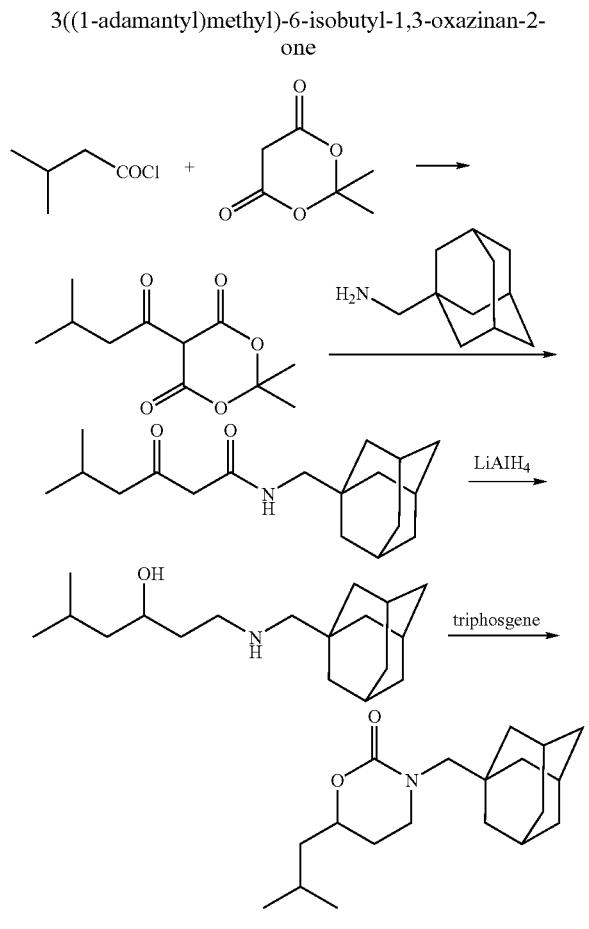

Step 1

To a solution of 2,2-dimethyl-1,3-dioxane-4,6-dione (14.4 g, 0.1 mol) and pyridine (19.4 mL) in CH$_2$Cl$_2$ (150 mL) at 0° C., a solution of 3-methylbutyryl chloride (12 g, 0.1 mmol) in CH$_2$Cl$_2$ (140 mL) was added slowly. The reaction mixture was stirred for 1 h at 0° C. and for a further 1 h at rt. The mixture was concentrated to give a residue, which was diluted with EtOAc (500 mL) and filtered. The filtrate was washed with 10% aq Na$_2$CO$_3$ (200 mL) and water (200 mL). The combined aqueous layers were extracted with EtOAc (100 mL). The combined organic layers were washed with brine (100 mL), dried over MgSO$_4$ and concentrated to give crude 5-(3-methylbutanoyl)-2,2-dimethyl-1,3-dioxane-4,6-dione (26 g), which was used in the next step without further purification.

Step 2

A solution of 5-(3-methylbutanoyl)-2,2-dimethyl-1,3-dioxane-4,6-dione (2.76 g, 12 mmol) and (1-adamantylmethyl)amine (2 g, 12 mmol) in anhydrous 1,4-dioxane (10 mL) was heated under reflux for 2 h. Solvent was removed in vacuo. The residue was diluted with EtOAc (50 mL), washed with water, aq K$_2$CO$_3$ and brine, dried over Na$_2$SO$_4$ and concentrated to dryness. The residue was purified by chromatography on a silica gel column eluted with 20:1 PE/EtOAc to give the N-(1-adamantylmethyl)-5-methyl-3-oxohexanamide (1.90 g, 54.4%). $^1$H NMR: (400 MHz, CDCl$_3$): δ=0.92 (s, 3H), 0.96 (s, 3H), 1.54 (s, 7H), 1.62-1.73 (m, 9H), 1.98 (s, 4H), 2.12 (m, 1H), 2.45 (d, 2H), 2.95 (d, 2H), 3.65 (s, 2H).

Step 3

A solution of N-(1-adamantylmethyl)-5-methyl-3-oxohexanamide (1.5 g, 5.1 mmol) in anhydrous THF (15 mL) was added slowly to a suspension of LAH (500 mg, 13.1 mmol) in anhydrous THF (5 mL) under N$_2$ at 0° C. The reaction mixture was heated to 70° C. and stirred at this temperature overnight. Water (0.5 mL) and 10% aq NaOH (0.5 mL) were added to quench the reaction. The resulting slurry was filtered. The filtrate was concentrated in vacuo and the residue was purified by chromatography on a silica gel column eluted with 10:1 PE/EtOAc to give 1-(1-adamantylmethylamino)-5-methyl-hexan-3-ol (900 mg, 63.3%). MS (M+1): 280.

Step 4

A solution of triphosgene (35 mg, 0.12 mmol) in anhydrous CH$_2$Cl$_2$ (500 μL) was added slowly to a solution of 1-(1-adamantylmethylamino)-5-methylhexan-3-ol (100 mg, 0.36 mmol) and Et$_3$N (50 μl, 0.257 mmol) in anhydrous CH$_2$Cl$_2$ (2 mL) at 0° C. The reaction mixture was stirred for 1 h. Solvent was removed and the residue was purified by preparative TLC to give 3-((1-adamantyl)methyl)-6-isobutyl-1,3-oxazinan-2-one (80 mg, 74%). $^1$H NMR (MeOD, 400 MH$_Z$): δ=0.93-0.98 (q, 6H), 1.35-1.44 (m, 1H), 1.50-2.08 (m, 18H), 2.87-2.94 (d, 1H), 3.12-3.20 (d, 1H), 3.30-3.40 (m, 1H), 3.49-3.61 (m, 1H), 4.35-4.45 (m, 1H); MS m/z=306.

Example 24

(S)-1-((1-adamantyl)methyl)-4-(hydroxymethyl)imidazolidin-2-one

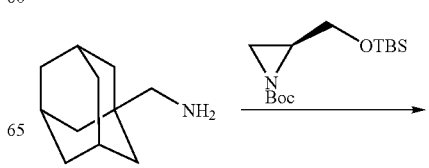

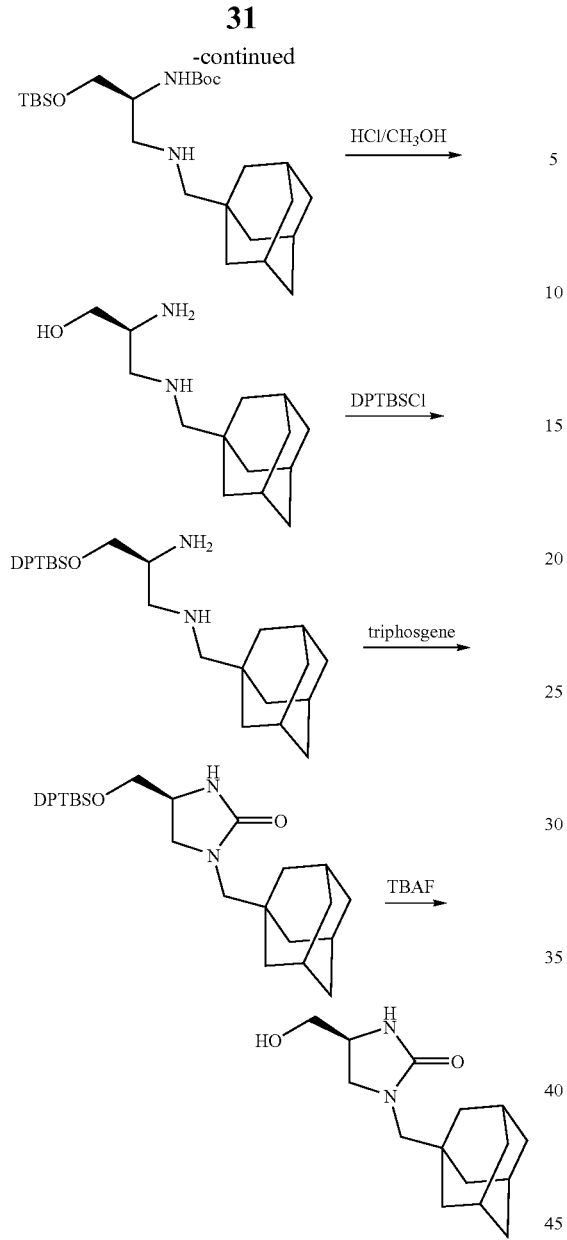

Step 1

To a solution of (1-adamantylmethyl)amine (15 g, 52 mmol) in anhydrous $CH_2Cl_2$ (50 mL) was added tert-butyl 2-((tert-butyldimethylsilyloxy)methyl)aziridine-1-carboxylate (13 g, 78.3 mmol). The mixture was stirred for 10 min, the solvent was removed in vacuo and the residue was stirred at 40° C. for 5 h. The mixture was diluted with EtOAc (500 mL) and washed with water (100 mL), 1N aq HCl (50 mL), satd aq $NaHCO_3$ (50 ml) and brine (50 mL), and dried over $MgSO_4$. The solution was concentrated to give a residue, which was purified by chromatography on silica gel to give (S)-tert-butyl 1-(tert-butyldimethylsilyloxy)-3-((1-adamantylmethyl)amino)propan-2-ylcarbamate (10 g, 24%). $^1H$ NMR: ($CDCl_3$, 400 MHz): δ=0.041 (s, 6H), 0.882 (s, 9H), 1.44 (s, 9H), 1.49 (s, 6H), 1.65 (m, 6H), 1.94 (s, 3H), 2.23 (s, 2H), 2.62-2.81 (m, 2H), 3.67 (m, 3H), 5.30 (s, 1H).

Step 2

A solution of (S)-tert-butyl 1-(tert-butyldimethylsilyloxy)-3-((1-adamantylmethyl)amino)propan-2-ylcarbamate (10 g, 22 mmol) in 1N HCl in $CH_3OH$ (30 mL) was stirred for 3 h at rt. After the reaction was complete, the solution was concentrated to give crude (S)-2-amino-3-((1-adamantylmethyl)amino)propan-1-ol as its HCl salt, which was used for the next step without purification.

Step 3

To a solution of (S)-2-amino-3-((1-adamantylmethyl)amino)propan-1-ol HCl salt (1.2 g, 3.8 mmol) in anhydrous $CH_2Cl_2$ (20 mL) were added DIEA (1.9 g, 15.2 mmol), DMAP (2.3 mg, 0.02 mmol) and TBDPSCl (1.2 g, 4.2 mmol) at 0° C. The mixture was stirred at rt for 2 h. The reaction solution was extracted with $CH_2Cl_2$ (100 mL) and water (20 mL). The organic layer was washed with brine (20 mL), dried over $MgSO_4$, and concentrated to give the crude product, which was purified by preparative TLC (PE:EtOAc 10/1) to afford (S)-3-(tert-butyldiphenylsilyloxy)-$N^1$-(1-adamantylmethyl)propane-1,2-diamine (620 mg, 29%) $^1H$ NMR: ($CDCl_3$, 400 MHz): δ=1.05 (s, 9H), 1.54 (s, 6H), 1.62-1.73 (m, 6H), 1.98 (s, 3H), 2.32 (d, 1H), 2.45 (d, 1H), 2.56 (d, 1H), 2.85 (d, 1H), 3.15 (m, 4H), 3.65 (m, 2H), 7.4 (m, 6H), 7.62 (m, 4H).

Step 4

A solution of triphosgene (124 mg, 0.42 mmol) in anhydrous $CH_2Cl_2$ (2 mL) was added slowly to a solution of (S)-3-(tert-butyldiphenylsilyloxy)-$N^1$-(1-adamantylmethyl)propane-1,2-diamine (600 mg, 1.26 mmol) and triethylamine (140 mg, 1.4 mmol) in anhydrous $CH_2Cl_2$ (10 mL) at 0° C. The reaction mixture was stirred for another 1 h. The mixture was diluted with water and extracted with $CH_2Cl_2$ (50 mL). The organic layer was washed with 0.1 N aq HCl (2×20 mL) and brine (10 mL), dried over $MgSO_4$ and concentrated to give a residue, which was purified by preparative TLC to provide (S)-4-((tert-butyldiphenylsilyloxy)methyl)-1-(1-adamantylmethyl)imidazolidin-2-one (330 mg, 52%). $^1H$ NMR: ($CDCl_3$, 400 MHz): δ=1.05 (s, 9H), 1.54 (s, 6H), 1.62-1.73 (m, 8H), 1.98 (s, 3H), 2.77 (m, 2H), 3.21 (m, 1H), 3.55 (t, 1H), 3.65 (m, 2H), 3.82 (m, 1H), 4.57 (s, 1H), 7.4 (m, 6H), 7.62 (m, 4H).

Step 5

TBAF (400 mg, 1.6 mmol) was added to a solution of (S)-4-((tert-butyldiphenylsilyloxy)methyl)-1-(1-adamantylmethyl)imidazolidin-2-one (261 mg, 0.52 mmol) in anhydrous THF (5 mL) at 0° C. The reaction was stirred at rt overnight. The reaction solution was concentrated to give the residue, which was purified by preparative TLC (PE/EtOAc 1/1) to provide (S)-1-(1-adamantylmethyl)-4-(hydroxymethyl)imidazolidin-2-one (45 mg, 10%). $^1H$ NMR: ($CDCl_3$, 400 MHz): δ=1.54 (s, 6H), 1.62-1.73 (m, 6H), 1.98 (s, 3H), 2.77 (m, 2H), 3.35 (m, 1H), 3.55-3.75 (m, 3H), 3.82 (m, 1H); MS m/z=265

Example 25

(4R,5S)-3-((1-adamantyl)methyl)-4-methyl-5-phenyloxazolidin-2-one

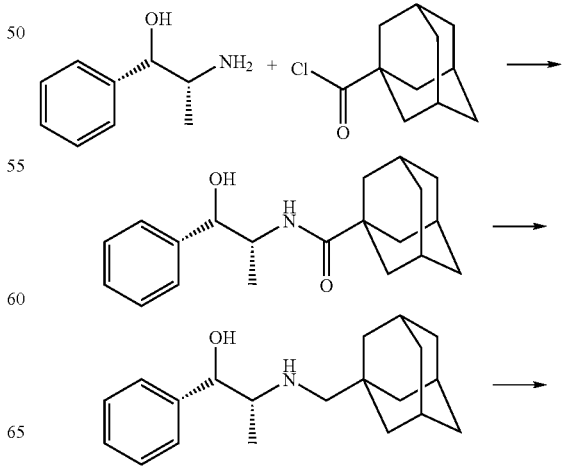

-continued

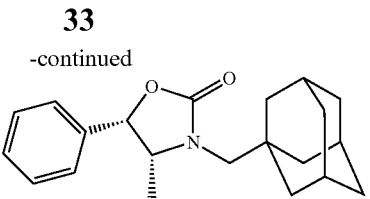

Step 1

To an ice-cold, stirred solution of (1S,2R)-2-amino-1-phenylpropan-1-ol (1.50 g, 9.9 mmol), DIEA (4.4 mL, 24.8 mmol) in CH₂Cl₂ (50 mL) was added solid adamantane-1-carbonyl chloride (4.34 g, 21.8 mmol). The mixture was stirred overnight, diluted with ether (150 mL), washed with 5% aq HCl (50 mL) and satd aq NaHCO₃ (50 mL) and dried over MgSO₄. Removal over the solvent afforded a foam (4.78 g), which was dissolved in THF (50 mL) and MeOH (100 mL). 5% aq NaOH (50 mL) was added and the mixture was stirred at rt for 4 h. The mixture was rotovaped to remove the organic solvents and the aqueous residue was extracted with EtOAc (150 mL). The EtOAc extract was washed with brine (50 mL), dried over MgSO₄ and concentrated to afford N-((1S,2R)-1-hydroxy-1-phenylpropan-2-yl)adamantane-1-carboxamide (3.07 g, 98%) as a sticky off-white solid. LC-MS (3 min) $t_R$=1.78 min, m/z=314, 296.

Step 2

A stirred solution of N-((1S,2R)-1-hydroxy-1-phenylpropan-2-yl)adamantane-1-carboxamide (3.07 g, 9.8 mmol) in dry THF (50 mL) was cooled in an ice bath and 1M BH₃ in THF (50 mL, 50 mmol) was added. The ice bath was allowed to melt and the mixture was stirred over the weekend at rt. The mixture was poured into 5% aq HCl (50 mL). The mixture was concentrated on the rotary evaporator to leave a white solid which was taken up in 5% aq HCl (75 mL) and washed with ether (150 mL). The aqueous layer was made strongly basic by addition of NaOH and extracted with EtOAc (2×100 mL). The combined EtOAc extracts were dried over MgSO₄ and concentrated to afford (1S,2R)-2-(1-adamantylmethylamino)-1-phenylpropan-1-ol (2.28 g, 77%) as an oil. LC-MS (3 min) $t_R$=1.32 min, m/z=300.

Step 3

To an ice-cold, stirred solution of (1S,2R)-2-(1-adamantylmethylamino)-1-phenylpropan-1-ol (715 mg, 2.4 mmol) and DIEA (1.3 mL, 7.2 mmol) in CH₂Cl₂ (50 mL) was added solid triphosgene (233 mg, 0.79 mmol). The ice bath was allowed to melt and the mixture was stirred at rt for 3 h. The mixture was diluted with ether (150 mL), washed with 5% aq HCl (50 mL) and satd aq NaHCO₃ (50 mL), and dried over MgSO₄. Removal of the solvent left (4R,5S)-3-((1-adamantyl)methyl)-4-methyl-5-phenyloxazolidin-2-one as a white solid. ¹H NMR (CDCl₃) 0.76 (d, 3H), 1.5-1.8 (12H), 2.01 (3H), 2.52 (d, 1H), 3.30 (d, 1H), 4.09 (m, 1H), 5.63 (d, 1H), 7.25-7.40 (5H); LC-MS (3 min) $t_R$=2.26 min, m/z=326, 348.

Example 26

3-((1-adamantyl)methyl)-6-methyl-1,3-oxazinan-2-one

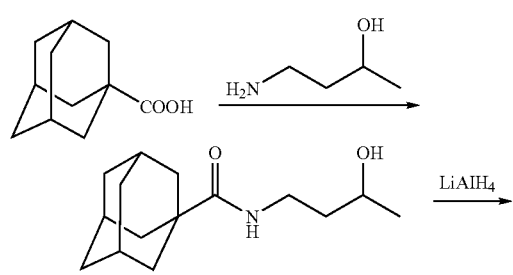

-continued

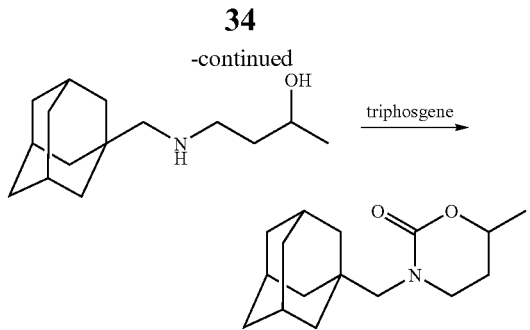

Step 1

Adamantane-1-carboxylic acid (404 mg, 2.24 mmol), 4-amino-butan-2-ol (200 mg, 2.24 mmol), EDCI (885 mg, 4.48 mmol) and HOBt (605 mg, 4.48 mmol) were dissolved in anhydrous CH₂Cl₂. DIEA (1.444 g, 11.2 mmol) was added to the above mixture at 0° C. under nitrogen. The mixture was stirred overnight and concentrated to give a residue, which was purified by preparative TLC to provide N-(3-hydroxybutyl)adamantane-1-carboxamide (170 mg, 30%). ¹H NMR (MeOD, 400 MHz): δ=1.20 (d, 3H), 1.66~2.04 (m, 17H), 2.87 (m, 2H), 3.79(m, 1H).

Step 2

To a suspension of LiAlH₄ (51 mg, 1.36 mmol) in THF (1.5 mL) was added a solution of N-(3-hydroxybutyl)adamantane-1-carboxamide (170 mg, 0.68 mmol) in THF at 0° C. The mixture was stirred and heated under reflux overnight. The reaction was quenched with H₂O (2 mL). The mixture was filtered to give 4-(1-adamantylmethylamino)butan-2-ol (50 mg, 31%). ¹H NMR (CD₃OD, 400 MHz): δ=1.12 (d, 3H), 1.58~1.88 (m, 17H) 2.28 (t, 2H), 2.65 (m, 2H), 3.79 (m, 1H).

Step 3

To a solution of 4-(1-adamantylmethylamino)butan-2-ol (50 mg, 0.21 mmol) and Et₃N (42.4 mg, 0.42 mmol) in CH₂Cl₂ (5 mL) at 0° C. under N₂, a solution of triphosgene (25 mg, 0.084 mmol) in CH₂Cl₂ (1 mL) was added dropwise. The mixture was stirred at rt for 1 h. The mixture was concentrated to give crude product, which was purified by preparative TLC to afford 3-((1-adamantyl)methyl)-6-methyl-1,3-oxazinan-2-one (12 mg, 21%). ¹H NMR (CD₃OD, 400 MHz): δ=1.46 (d, 3H), 1.72~2.18 (m, 17H), 3.02 (d, 1H), 3.34 (d, 1H), 3.44 (m, 1H), 3.63 (m, 1H), 4.58 (m, 1H); MS m/z=264

Example 27

(S)-1-(2-adamantyl)-4-tert-butylimidazolidin-2-one

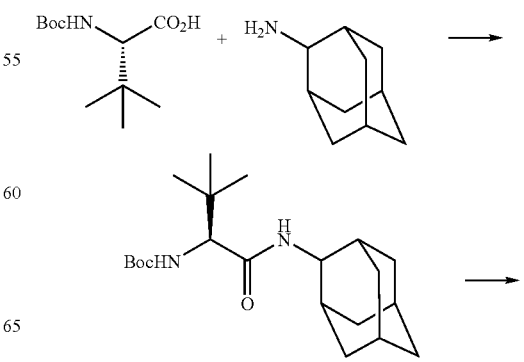

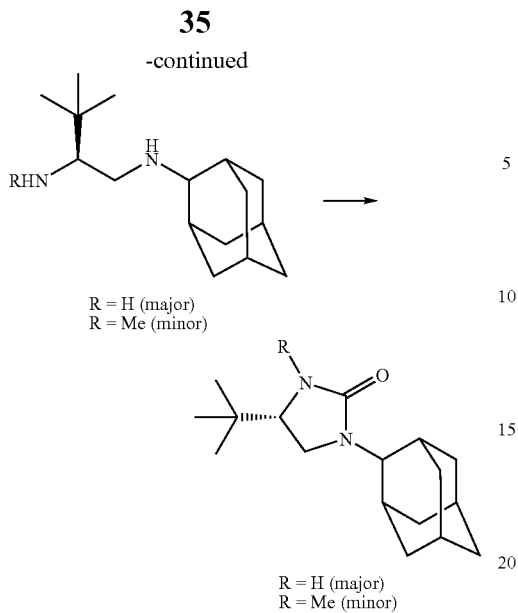

R = H (major)
R = Me (minor)

↓

R = H (major)
R = Me (minor)

Step 1

To a stirred slurry of Boc-t-Leu-OH (1.59 g, 6.8 mmol), 2-aminoadamantane hydrochloride (1.28 g, 6.8 mmol) and DIEA (3.0 mL, 17.0 mmol) in $CH_2Cl_2$ (30 mL) was added solid HATU (2.86 g, 7.5 mmol). The mixture was stirred overnight at rt, diluted with ether (150 mL), washed with 5% aq HCl (50 mL) and satd aq $NaHCO_3$ (50 mL) and dried over $MgSO_4$. Removal of the solvent left crude (S)-tert-butyl 1-(2-adamantylamino)-3,3-dimethyl-1-oxobutan-2-ylcarbamate (2.08 g, 83%) as a tan solid. LC-MS (3 min) $t_R$=2.17 min, m/z=365.

Step 2

A stirred solution of crude (S)-tert-butyl 1-(2-adamantylamino)-3,3-dimethyl-1-oxobutan-2-ylcarbamate (2.08 g, 5.7 mmol) in dry THF (20 mL) was cooled in an ice bath and 1M $BH_3$ in THF (40 mL, 40 mmol) was added. The mixture was stirred at rt overnight and poured into 10% aq $NaHCO_3$ (200 mL). the mixture was extracted with EtOAc (2×100 mL). The combined EtOAc extracts were washed with brine (100 mL), dried over $MgSO_4$ and concentrated to afford a white solid (1.84 g). This material was dissolved in was dissolved in $CH_2Cl_2$ (30 mL) and TFA (5 mL) was added. After stirring for 1.5 h, satd aq $NaHCO_3$ (100 mL) was added and the mixture was extracted with $CH_2Cl_2$ (3×50 mL). The combined $CH_2Cl_2$ extracts were dried over $Na_2SO_4$ and concentrated to leave a white solid (1.92 g,) which was used without purification in the next step. LC-MS showed the presence of (S)—$N^1$-(2-adamantyl)-3,3-dimethylbutane-1,2-diamine LC-MS (3 min) $t_R$=0.74 min, m/z=251 and (S)—$N^1$-(2-adamantyl)-$N^2$,3,3-trimethylbutane-1,2-diamine LC-MS (3 min) $t_R$=1.16 min, m/z=265.

Step 3

A stirred solution of crude product from Step 2 (793 mg, 3.17 mmol) and DIEA (2 mL, 11.1 mmol) in $CH_2Cl_2$ (20 mL) was cooled in an ice bath and solid triphosgene (310 mg, 1.05 mmol) was added. The ice bath was allowed to melt. The mixture was stirred overnight at rt, diluted with ether (80 mL), washed with 5% aq HCl (2×20 mL) and satd aq $NaHCO_3$ (20 mL) and dried over $MgSO_4$. Removal of the solvent left a syrup (0.80 g). Chromatography on a 40-g silica gel cartridge eluted with a 0-100% EtOAc in hexanes gradient afforded (S)-4-tert-butyl-1-(2-adamantyl)imidazolidin-2-one (80 mg) as a white solid. $^1$H NMR ($CDCl_3$) 0.90 (s, 9H), 1.5-2.0 (12H), 2.27 (s, 1H), 2.39 (s, 1H), 3.35 (m, 2H), 3.58 (t, 1H), 3.63 (s, 1H), 4.42 (s, 1H); LC-MS (3 min) $t_R$=2.01 min, m/z=277. A mixed fraction (171 mg) containing crude (S)-1-(2-adamantyl)-4-tert-butyl-3-methylimidazolidin-2-one was also isolated.

Example 28

(S)-1-(2-adamantyl)-4-tert-butyl-3-methylimidazolidin-2-one

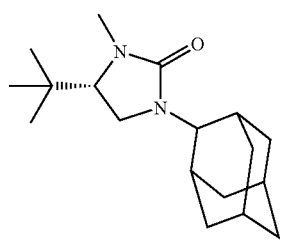 [SMILES: CN1C(=O)N(C2C3CC4CC(C3)CC2C4)C[C@@H]1C(C)(C)C]

A portion of the mixed fraction from Example 27 Step 3 was purified by preparative HPLC to give (S)-1-(2-adamantyl)-4-tert-butyl-3-methylimidazolidin-2-one (1.2 mg). $^1$H NMR ($CDCl_3$) 0.96 (s, 9H), 1.5-2.0 (12H), 2.36 (br s, 1H), 2.39 (br s, 1H), 2.89 (s, 3H), 3.06 (dd, 1H), 3.21 (dd, 1H), 3.42 (t, 1H), 3.58 (s, 1H); LC-MS (3 min) $t_R$=2.21 min, m/z=291.

Example 29

(±)-5-(4-bromophenyl)-3-(2-adamantyl)oxazolidin-2-one

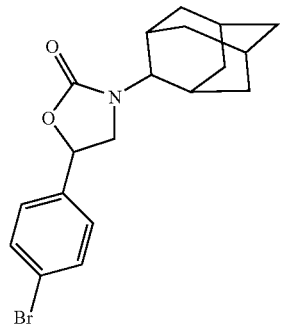 [SMILES: O=C1OC(c2ccc(Br)cc2)CN1C1C2CC3CC(C2)CC1C3]

The title compound was prepared following procedures analogous to those described in Example 17 Steps 3 and 5 using 4-bromostyrene and 2-aminoadamantane. $^1$H NMR ($CDCl_3$) 1.6-2.0 (12H), 2.28 (s, 1H), 2.44 (s, 1H), 3.52 (t, 1H), 3.75 (s, 1H), 4.09 (t, 1H), 5.41 (t, 1H), 7.24 (d, 2H), 7.53 (d, 2H); LC-MS (3 min) $t_R$=2.22 min, m/z=376, 378.

Example 30

(S)-1-(1-adamantyl)-4-phenylimidazolidin-2-one

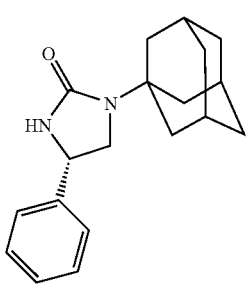 [SMILES: O=C1N[C@@H](c2ccccc2)CN1C12CC3CC(CC(C3)C1)C2]

The title compound was prepared following procedures analogous to those described in Example 27 using (S)-Boc-Phg-OH. $^1$H NMR (MeOD, 400 MH$_z$): δ 1.6-2.2 (15H), 3.25 (m, 1H), 3.90 (m, 1H), 4.14 (m, 1H), 7.2-7.4 (5H); MS m/z=297.

Example 31

(±)-4-tert-butyl-1-(2-adamantyl)tetrahydropyrimidin-2(1H)-one

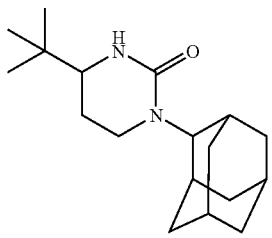 [SMILES: CC(C)(C)C1CCN(C2C3CC4CC(C3)CC2C4)C(=O)N1]

The title compound was prepared following procedures analogous to those described in Example 27 using (±)-3-(tert-butoxycarbonylamino)-4,4-dimethylpentanoic acid. $^1$H NMR (CDCl$_3$) 5.34 (br s, 1H), 4.09(s, 1H), 3.64(m, 1H), 3.31(td, 1H), 3.07(m, 1H), 2.19(s, 2H), 1.98-1.74(m, 10H), 1.72(s, 2H), 1.64(m, 4H), 0.97(s, 9H); LC-MS (3 min) t$_R$=2.07 min, m/z=291.

Example 32

(S)-4-cyclohexyl-1-(2-adamantyl)imidazolidin-2-one

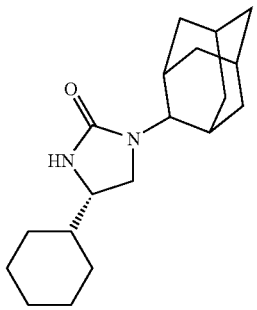 [SMILES: O=C1N[C@@H](C2CCCCC2)CN1C1C2CC3CC(C2)CC1C3]

The title compound was prepared following procedures analogous to those described in Example 27 using (S)-Boc-cyclohexylglycine. MS m/z=303.

Example 33

(S)-4-isopropyl-1-(2-adamantyl)imidazolidin-2-one

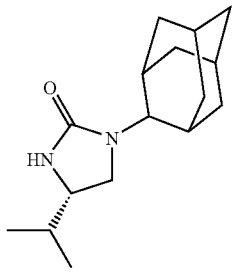 [SMILES: CC(C)[C@H]1CN(C2C3CC4CC(C3)CC2C4)C(=O)N1]

The title compound was prepared following procedures analogous to those described in Example 27 using (S)-Boc-Val-OH. MS m/z=263.

Example 34

(±)-5-(3-bromophenyl)-3-(2-adamantyl)oxazolidin-2-one

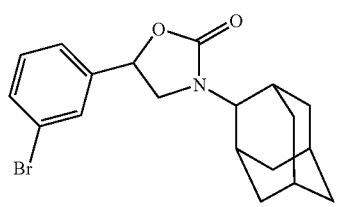 [SMILES: O=C1OC(c2cccc(Br)c2)CN1C1C2CC3CC(C2)CC1C3]

The title compound was prepared following procedures analogous to those described in Example 17 Steps 3 and 5 using 3-bromostyrene and 2-aminoadamantane. 1.60-2.00 (12H), 2.27 (s, 1H), 2.47 (s, 1H), 3.54 (t, 1H), 3.74 (s, 1H), 4.09 (t, 1H), 5.42 (t, 1H), 7.20-7.60 (4H). LC-MS (3 min) t$_R$=2.20 min, m/z=376, 378.

Example 35

(±)-1-(2-adamantyl)-4-(hydroxymethyl)-4-isobutyl-imidazolidin-2-one

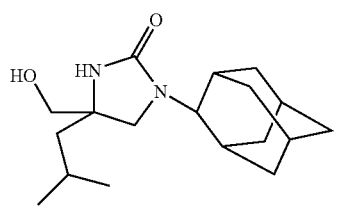 [SMILES: CC(C)CC1(CO)CN(C2C3CC4CC(C3)CC2C4)C(=O)N1]

The title compound was prepared following procedures analogous to those described in Example 27 using (±)-2-(tert-butoxycarbonylamino)-2-(hydroxymethyl)-4-methylpentanoic acid. MS m/z=307.

Example 36

(±)-1-(1-adamantylmethyl)-4-(hydroxymethyl)-4-isobutylimidazolidin-2-one

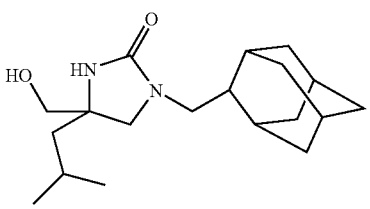 [SMILES: CC(C)CC1(CO)CN(CC2C3CC4CC(C3)CC2C4)C(=O)N1]

The title compound was prepared following procedures analogous to those described in Example 27 using (±)-2-(tert-butoxycarbonylamino)-2-(hydroxymethyl)-4-methylpentanoic acid and 1-(aminomethyl)adamantane. MS m/z=321.

Example 37

(±)-5-(biphenyl-3-yl)-3-(2-adamantyl)oxazolidin-2-one

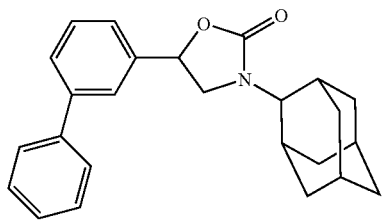 [SMILES: O=C1OC(c2cccc(-c3ccccc3)c2)CN1C1C2CC3CC(C2)CC1C3]

A mixture of (±)-5-(3-bromophenyl)-3-(2-adamantyl)oxazolidin-2-one (65 mg, 0.17 mmol), PhB(OH)$_2$ (32 mg, 0.26 mmol) and n-PrOH (2 mL) was stirred at it under an N$_2$ atmosphere for 0.5 h. Solid Pd(OAac)$_2$ (2 mg, 0.009 mmol) and PPh$_3$ (7 mg, 0.027 mmol) were added followed by a solution of Na$_2$CO$_3$ (28 mg, 0.26 mmol) in water (1 mL). The mixture was heated at reflux for 1 h. The mixture was cooled, diluted with ether (150 mL), washed with 1M aq NaOH (50 mL), dried over MgSO$_4$ and concentrated to leave a brown residue (69 mg). The residue was applied to a 2-g silica cartridge and eluted sequentially with 0, 10, 25, 50, 75 and 100% EtOAc in hexanes (15 mL of each) to give 6 fractions. Fraction 3 was concentrated to afford the title compound as an oil. $^1$H NMR (CDCl$_3$) δ 1.60-2.00 (12H), 2.26 (s, 1H), 2.48 (s, 1H), 3.61 (t, 1H), 3.75 (s, 1H), 4.12 (t, 1H), 5.52 (t, 1H), 7.30-7.65 (9H). LC-MS (3 min) t$_R$=2.24 min, m/z=374.

Example 38

(±)-5-(biphenyl-4-yl)-3-(2-adamantyl)oxazolidin-2-one

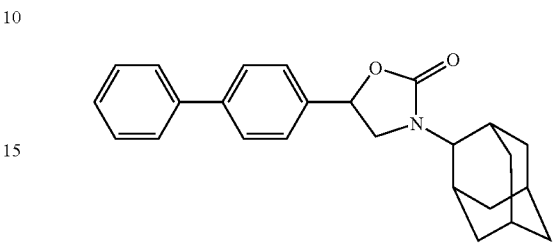

The title compound was prepared following procedures analogous to those described in Example 37 using (±)-5-(4-bromophenyl)-3-(2-adamantyl)oxazolidin-2-one. $^1$H NMR (CDCl$_3$) δ 1.60-2.00 (12H), 2.28 (s, 1H), 2.48 (s, 1H), 3.60 (t, 1H), 3.77 (s, 1H), 4.13 (t, 1H), 5.49 (t, 1H), 7.30-7.65 (9H). LC-MS (3 min) t$_R$=2.30 min, m/z=374.

Prophetic Examples

The following Tables 1-7 provide additional examples of those compounds of the invention that could be prepared by the methods described herein.

TABLE 1

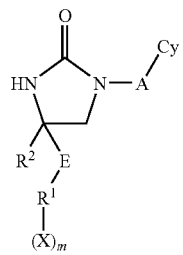

Ia

| Example No. | E | R$^1$—(X)$_m$ | R$^2$ | A | Cy |
|---|---|---|---|---|---|
| PE1 | bond | i-Pr | H | bond | 1-adamantyl |
| PE2 | bond | cyclohexyl | H | bond | 1-adamantyl |
| PE3 | bond | i-Bu | CH$_2$OH | bond | 1-adamantyl |
| PE4 | bond | t-Bu | Me | bond | 1-adamantyl |
| PE5 | bond | i-Pr | H | bond | 2-adamantyl |
| PE6 | bond | cyclohexyl | H | bond | 2-adamantyl |
| PE7 | bond | i-Bu | CH$_2$OH | bond | 2-adamantyl |
| PE8 | bond | t-Bu | Me | bond | 2-adamantyl |
| PE9 | bond | i-Pr | H | bond | 1-adamantyl |
| PE10 | bond | cyclohexyl | H | CH$_2$ | 1-adamantyl |
| PE11 | bond | i-Bu | CH$_2$OH | CH$_2$ | 1-adamantyl |
| PE12 | bond | t-Bu | Me | CH$_2$ | 1-adamantyl |

TABLE 1-continued

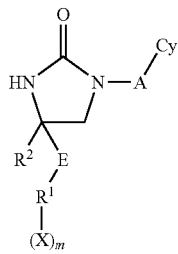

Ia

| Example No. | E | R¹—(X)ₘ | R² | A | Cy |
|---|---|---|---|---|---|
| PE13 | bond | 3-biphenyl | Me | bond | 2-adamantyl |
| PE14 | bond | 4-biphenyl | Me | bond | 2-adamantyl |
| PE15 | bond | 3-(3-pyridyl)phenyl | Me | bond | 2-adamantyl |
| PE16 | bond | 3-(1-oxo-4-pyridyl)phenyl | Me | bond | 2-adamantyl |
| PE17 | bond | 3-(2-carboxyphenyl)phenyl | Me | bond | 2-adamantyl |
| PE18 | bond | 3-(3-carboxyphenyl)phenyl | Me | bond | 2-adamantyl |
| PE19 | bond | 3-(2-methylsulfonylphenyl)phenyl | Me | bond | 2-adamantyl |
| PE20 | bond | 3-(3-methylsulfonylphenyl)phenyl | Me | bond | 2-adamantyl |
|  | bond | 4-F-Ph | $CH_2CH_2OH$ | $CH_2$ | 1-adamantyl |
|  | bond | 2-F-Ph | $CH_2CH_2CH_2OH$ | $CH_2$ | 1-adamantyl |
|  | bond | Ph | $CH_2CMe_2OH$ | $CH_2$ | 1-adamantyl |
|  | bond | Ph | $CH_2CH_2CONH_2$ | $CH_2$ | 1-adamantyl |
|  | bond | 4-F-Ph | $CH_2CH_2CH_2NHSO_2Me$ | $CH_2$ | 1-adamantyl |
|  | bond | 2-FPh | $CH_2CH_2CONH_2$ | $CH_2$ | 1-adamantyl |
|  | bond | Ph | $CH_2CH_2N(CH_2CH_2)_2O$ | $CH_2$ | 1-adamantyl |

TABLE 2

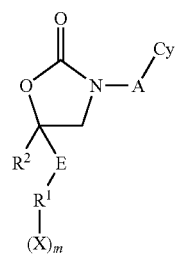

Ib

| Example No. | E | R¹—(X)ₘ | R² | A | Cy |
|---|---|---|---|---|---|
| PE21 | bond | i-Pr | Me | bond | 1-adamantyl |
| PE22 | bond | cyclohexyl | Me | bond | 1-adamantyl |
| PE23 | bond | i-Bu | Me | bond | 1-adamantyl |
| PE24 | bond | i-Pr | Me | bond | 2-adamantyl |
| PE25 | bond | cyclohexyl | Me | bond | 2-adamantyl |

TABLE 2-continued

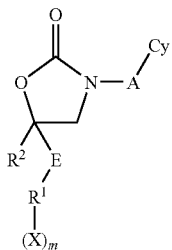

| Example No. | E | $R^1$—$(X)_m$ | $R^2$ | A | Cy |
|---|---|---|---|---|---|
| PE26 | bond | t-Bu | Me | bond | 2-adamantyl |
| PE27 | bond | i-Pr | Me | bond | 1-adamantyl |
| PE28 | bond | cyclohexyl | Me | $CH_2$ | 1-adamantyl |
| PE29 | bond | t-Bu | Me | $CH_2$ | 1-adamantyl |
| PE30 | bond | 3-biphenyl | Me | bond | 2-adamantyl |
| PE31 | bond | 4-biphenyl | Me | bond | 2-adamantyl |
| PE32 | bond | 3-(1-oxo-3-pyridyl)phenyl | Me | bond | 2-adamantyl |
| PE33 | bond | 3-(4-pyridyl)phenyl | Me | bond | 2-adamantyl |
| PE34 | bond | 3-(2-carboxyphenyl)phenyl | Me | bond | 2-adamantyl |
| PE35 | bond | 3-(3-carboxyphenyl)phenyl | Me | bond | 2-adamantyl |
| PE36 | bond | 3-(2-methylsulfonylphenyl)phenyl | Me | bond | 2-adamantyl |
| PE37 | bond | 3-(3-methylsulfonylphenyl)phenyl | Me | bond | 2-adamantyl |
| | bond | 4-F-Ph | $CH_2CH_2OH$ | $CH_2$ | 1-adamantyl |
| | bond | 2-F-Ph | $CH_2CH_2CH_2OH$ | $CH_2$ | 1-adamantyl |
| | bond | Ph | $CH_2CMe_2OH$ | $CH_2$ | 1-adamantyl |
| | bond | Ph | $CH_2CH_2CONH_2$ | $CH_2$ | 1-adamantyl |
| | bond | 4-F-Ph | $CH_2CH_2CH_2NHSO_2Me$ | $CH_2$ | 1-adamantyl |
| | bond | 2-F-Ph | $CH_2CH_2CONH_2$ | $CH_2$ | 1-adamantyl |
| | bond | Ph | $CH_2CH_2N(CH_2CH_2)_2O$ | $CH_2$ | 1-adamantyl |
| | bond | 4-(4-F-Ph)-Ph | $CH_2CH_2OH$ | bond | 2-adamantyl |
| | bond | 4-(2-Me-4-pyridyl)-Ph | $CH_2CH_2CH_2OH$ | bond | 2-adamantyl |
| | bond | 4-(1-Me-6-oxo-3-pyridyl)-pH | $CH_2CMe_2OH$ | bond | 2-adamantyl |
| | bond | 4-(4-F-Ph)-Ph | $CH_2CH_2CONH_2$ | bond | 2-adamantyl |
| | bond | 4-(2-Me-4-pyridyl)-Ph | $CH_2CH_2CH_2NHSO_2Me$ | bond | 2-adamantyl |
| | bond | 4-(1-Me-6-oxo-3-pyridyl)-pH | $CH_2CH_2CONH_2$ | bond | 2-adamantyl |
| | bond | 4-(4-F-Ph)-Ph | $CH_2CH_2N(CH_2CH_2)_2O$ | bond | 2-adamantyl |

TABLE 3

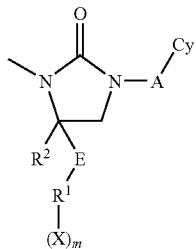

| Example No. | E | R¹—(X)ₘ | R² | A | Cy |
|---|---|---|---|---|---|
| PE41 | bond | i-Pr | H | bond | 1-adamantyl |
| PE42 | bond | cyclohexyl | H | bond | 1-adamantyl |
| PE43 | bond | i-Bu | CH₂OH | bond | 1-adamantyl |
| PE44 | bond | t-Bu | Me | bond | 1-adamantyl |
| PE45 | bond | i-Pr | H | bond | 2-adamantyl |
| PE46 | bond | cyclohexyl | H | bond | 2-adamantyl |
| PE47 | bond | i-Bu | CH₂OH | bond | 2-adamantyl |
| PE48 | bond | t-Bu | Me | bond | 2-adamantyl |
| PE49 | bond | i-Pr | H | bond | 1-adamantyl |
| PE50 | bond | cyclohexyl | H | CH₂ | 1-adamantyl |
| PE51 | bond | i-Bu | CH₂OH | CH₂ | 1-adamantyl |
| PE52 | bond | t-Bu | Me | CH₂ | 1-adamantyl |
| PE53 | bond | 3-biphenyl | Me | bond | 2-adamantyl |
| PE54 | bond | 4-biphenyl | Me | bond | 2-adamantyl |
| PE55 | bond | 3-(3-pyridyl)phenyl | Me | bond | 2-adamantyl |
| PE56 | bond | 3-(1-oxo-4-pyridyl)phenyl | Me | bond | 2-adamantyl |
| PE57 | bond | 3-(2-carboxyphenyl)phenyl | Me | bond | 2-adamantyl |
| PE58 | bond | 3-(3-carboxyphenyl)phenyl | Me | bond | 2-adamantyl |
| PE59 | bond | 3-(2-methylsulfonyl phenyl)phenyl | Me | bond | 2-adamantyl |
| PE60 | bond | 3-(3-methylsulfonyl phenyl)phenyl | Me | bond | 2-adamantyl |
| | bond | 4-F-Ph | CH₂CH₂OH | CH₂ | 1-adamantyl |
| | bond | 2-F-Ph | CH₂CH₂CH₂OH | CH₂ | 1-adamantyl |
| | bond | Ph | CH₂CMe₂OH | CH₂ | 1-adamantyl |
| | bond | Ph | CH₂CH₂CONH₂ | CH₂ | 1-adamantyl |
| | bond | 4-F-Ph | CH₂CH₂CH₂NHSO₂Me | CH₂ | 1-adamantyl |
| | bond | 2-F-Ph | CH₂CH₂CONH₂ | CH₂ | 1-adamantyl |
| | bond | Ph | CH₂CH₂N(CH₂CH₂)₂O | CH₂ | 1-adamantyl |
| | bond | 4-F-Ph | CH₂CH₂OH | CH₂ | 1-adamantyl |
| | bond | 2-F-Ph | CH₂CH₂CH₂OH | CH₂ | 1-adamantyl |
| | bond | Ph | CH₂CMe₂OH | CH₂ | 1-adamantyl |

TABLE 3-continued

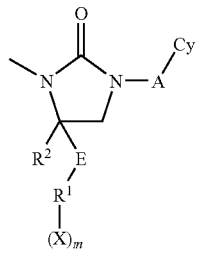

Ic

| Example No. | E | R¹—(X)ₘ | R² | A | Cy |
|---|---|---|---|---|---|
| | bond | Ph | $CH_2CH_2CONH_2$ | $CH_2$ | 1-adamantyl |
| | bond | 4-F-Ph | $CH_2CH_2CH_2NHSO_2Me$ | $CH_2$ | 1-adamantyl |
| | bond | 2-F-Ph | $CH_2CH_2CONH_2$ | $CH_2$ | 1-adamantyl |
| | bond | Ph | $CH_2CH_2N(CH_2CH_2)_2O$ | $CH_2$ | 1-adamantyl |

TABLE 4

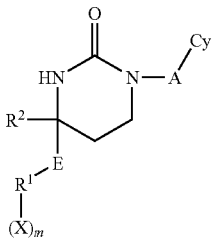

Id

| Example No. | E | R¹—(X)ₘ | R² | A | Cy |
|---|---|---|---|---|---|
| PE61 | bond | i-Pr | H | bond | 1-adamantyl |
| PE62 | bond | cyclohexyl | H | bond | 1-adamantyl |
| PE63 | bond | i-Bu | $CH_2OH$ | bond | 1-adamantyl |
| PE64 | bond | t-Bu | Me | bond | 1-adamantyl |
| PE65 | bond | i-Pr | H | bond | 2-adamantyl |
| PE66 | bond | cyclohexyl | H | bond | 2-adamantyl |
| PE67 | bond | i-Bu | $CH_2OH$ | bond | 2-adamantyl |
| PE68 | bond | t-Bu | Me | bond | 2-adamantyl |
| PE69 | bond | i-Pr | H | bond | 1-adamantyl |
| PE70 | bond | cyclohexyl | H | $CH_2$ | 1-adamantyl |
| PE71 | bond | i-Bu | $CH_2OH$ | $CH_2$ | 1-adamantyl |
| PE72 | bond | t-Bu | Me | $CH_2$ | 1-adamantyl |
| PE73 | bond | 3-biphenyl | Me | bond | 2-adamantyl |
| PE74 | bond | 4-biphenyl | Me | bond | 2-adamantyl |
| PE75 | bond | 3-(1-oxo-3-pyridyl)phenyl | Me | bond | 2-adamantyl |
| PE76 | bond | 3-(4-pyridyl)phenyl | Me | bond | 2-adamantyl |

TABLE 4-continued

Id

| Example No. | E | R¹—(X)$_m$ | R² | A | Cy |
|---|---|---|---|---|---|
| PE77 | bond | 3-(2-carboxyphenyl)phenyl | Me | bond | 2-adamantyl |
| PE78 | bond | 3-(3-carboxyphenyl)phenyl | Me | bond | 2-adamantyl |
| PE79 | bond | 3-(2-methylsulfonylphenyl)phenyl | Me | bond | 2-adamantyl |
| PE80 | bond | 3-(3-methylsulfonylphenyl)phenyl | Me | bond | 2-adamantyl |
| | bond | 4-F-Ph | CH$_2$CH$_2$OH | CH$_2$ | 1-adamantyl |
| | bond | 2-F-Ph | CH$_2$CH$_2$CH$_2$OH | CH$_2$ | 1-adamantyl |
| | bond | Ph | CH$_2$CMe$_2$OH | CH$_2$ | 1-adamantyl |
| | bond | Ph | CH$_2$CH$_2$CONH$_2$ | CH$_2$ | 1-adamantyl |
| | bond | 4-F-Ph | CH$_2$CH$_2$CH$_2$NHSO$_2$Me | CH$_2$ | 1-adamantyl |
| | bond | 2-F-Ph | CH$_2$CH$_2$CONH$_2$ | CH$_2$ | 1-adamantyl |
| | bond | Ph | CH$_2$CH$_2$N(CH$_2$CH$_2$)$_2$O | CH$_2$ | 1-adamantyl |
| | bond | 4-F-Ph | CH$_2$CH$_2$OH | CH$_2$ | 1-adamantyl |
| | bond | 2-F-Ph | CH$_2$CH$_2$CH$_2$OH | CH$_2$ | 1-adamantyl |
| | bond | Ph | CH$_2$CMe$_2$OH | CH$_2$ | 1-adamantyl |
| | bond | Ph | CH$_2$CH$_2$CONH$_2$ | CH$_2$ | 1-adamantyl |
| | bond | 4-F-Ph | CH$_2$CH$_2$CH$_2$NHSO$_2$Me | CH$_2$ | 1-adamantyl |
| | bond | 2-F-Ph | CH$_2$CH$_2$CONH$_2$ | CH$_2$ | 1-adamantyl |
| | bond | Ph | CH$_2$CH$_2$N(CH$_2$CH$_2$)$_2$O | CH$_2$ | 1-adamantyl |

TABLE 5

Ie

| Example No. | E | R¹—(X)$_m$ | R² | A | Cy |
|---|---|---|---|---|---|
| PE81 | bond | i-Pr | Me | bond | 1-adamantyl |
| PE82 | bond | cyclohexyl | Me | bond | 1-adamantyl |
| PE83 | bond | t-Bu | Me | bond | 1-adamantyl |

TABLE 5-continued

Ie

| Example No. | E | R¹—(X)ₘ | R² | A | Cy |
|---|---|---|---|---|---|
| PE84 | bond | i-Pr | Me | bond | 2-adamantyl |
| PE85 | bond | cyclohexyl | Me | bond | 2-adamantyl |
| PE86 | bond | t-Bu | Me | bond | 2-adamantyl |
| PE87 | bond | i-Pr | Me | bond | 1-adamantyl |
| PE88 | bond | cyclohexyl | Me | $CH_2$ | 1-adamantyl |
| PE89 | bond | t-Bu | Me | $CH_2$ | 1-adamantyl |
| PE90 | bond | 3-biphenyl | Me | bond | 2-adamantyl |
| PE91 | bond | 4-biphenyl | Me | bond | 2-adamantyl |
| PE92 | bond | 3-(3-pyridyl)phenyl | Me | bond | 2-adamantyl |
| PE93 | bond | 3-(1-oxo-4-pyridyl)phenyl | Me | bond | 2-adamantyl |
| PE94 | bond | 3-(2-carboxyphenyl)phenyl | Me | bond | 2-adamantyl |
| PE95 | bond | 3-(3-carboxylphenyl)phenyl | Me | bond | 2-adamantyl |
| PE96 | bond | 3-(2-methylsulfonyl phenyl)phenyl | Me | bond | 2-adamantyl |
| PE97 | bond | 3-(3-methylsulfonyl phenyl)phenyl | Me | bond | 2-adamantyl |
|  | bond | 4-F-Ph | $CH_2CH_2OH$ | $CH_2$ | 1-adamantyl |
|  | bond | 2-F-Ph | $CH_2CH_2CH_2OH$ | $CH_2$ | 1-adamantyl |
|  | bond | Ph | $CH_2CMe_2OH$ | $CH_2$ | 1-adamantyl |
|  | bond | Ph | $CH_2CH_2CONH_2$ | $CH_2$ | 1-adamantyl |
|  | bond | 4-F-Ph | $CH_2CH_2CH_2NHSO_2Me$ | $CH_2$ | 1-adamantyl |
|  | bond | 2-F-Ph | $CH_2CH_2CONH_2$ | $CH_2$ | 1-adamantyl |
|  | bond | Ph | $CH_2CH_2N(CH_2CH_2)_2O$ | $CH_2$ | 1-adamantyl |
|  | bond | 4-F-Ph | $CH_2CH_2OH$ | $CH_2$ | 1-adamantyl |
|  | bond | 2-F-Ph | $CH_2CH_2CH_2OH$ | $CH_2$ | 1-adamantyl |
|  | bond | Ph | $CH_2CMe_2OH$ | $CH_2$ | 1-adamantyl |
|  | bond | Ph | $CH_2CH_2CONH_2$ | $CH_2$ | 1-adamantyl |
|  | bond | 4-F-Ph | $CH_2CH_2CH_2NHSO_2Me$ | $CH_2$ | 1-adamantyl |
|  | bond | 2-F-Ph | $CH_2CH_2CONH_2$ | $CH_2$ | 1-adamantyl |
|  | bond | Ph | $CH_2CH_2N(CH_2CH_2)_2O$ | $CH_2$ | 1-adamantyl |

TABLE 6

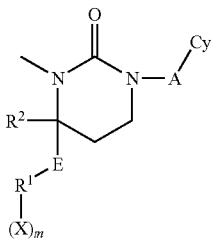

| Example No. | E | R¹—(X)ₘ | R² | A | Cy |
|---|---|---|---|---|---|
| PE101 | bond | i-Pr | H | bond | 1-adamantyl |
| PE102 | bond | cyclohexyl | H | bond | 1-adamantyl |
| PE103 | bond | i-Bu | CH₂OH | bond | 1-adamantyl |
| PE104 | bond | t-Bu | Me | bond | 1-adamantyl |
| PE105 | bond | i-Pr | H | bond | 2-adamantyl |
| PE106 | bond | cyclohexyl | H | bond | 2-adamantyl |
| PE107 | bond | i-Bu | CH₂OH | bond | 2-adamantyl |
| PE108 | bond | t-Bu | Me | bond | 2-adamantyl |
| PE109 | bond | i-Pr | H | bond | 1-adamantyl |
| PE110 | bond | cyclohexyl | H | CH₂ | 1-adamantyl |
| PE111 | bond | i-Bu | CH₂OH | CH₂ | 1-adamantyl |
| PE112 | bond | t-Bu | Me | CH₂ | 1-adamantyl |
| PE113 | bond | 3-biphenyl | Me | bond | 2-adamantyl |
| PE114 | bond | 4-biphenyl | Me | bond | 2-adamantyl |
| PE115 | bond | 3-(1-oxo-3-pyridyl)phenyl | Me | bond | 2-adamantyl |
| PE116 | bond | 3-(4-pyridyl)phenyl | Me | bond | 2-adamantyl |
| PE117 | bond | 3-(2-carboxylphenyl)phenyl | Me | bond | 2-adamantyl |
| PE118 | bond | 3-(3-carboxyphenyl)phenyl | Me | bond | 2-adamantyl |
| PE119 | bond | 3-(2-methysulfonyl phenyl)phenyl | Me | bond | 2-adamantyl |
| PE120 | bond | 3-(3-methylsulfonyl phenyl)phenyl | Me | bond | 2-adamantyl |
|  | bond | 4-F-Ph | CH₂CH₂OH | CH₂ | 1-adamantyl |
|  | bond | 2-F-Ph | CH₂CH₂CH₂OH | CH₂ | 1-adamantyl |
|  | bond | Ph | CH₂CMe₂OH | CH₂ | 1-adamantyl |
|  | bond | Ph | CH₂CH₂CONH₂ | CH₂ | 1-adamantyl |
|  | bond | 4-F-Ph | CH₂CH₂CH₂NHSO₂Me | CH₂ | 1-adamantyl |
|  | bond | 2-F-Ph | CH₂CH₂CONH₂ | CH₂ | 1-adamantyl |
|  | bond | Ph | CH₂CH₂N(CH₂CH₂)₂O | CH₂ | 1-adamantyl |
|  | bond | 4-F-Ph | CH₂CH₂OH | CH₂ | 1-adamantyl |
|  | bond | 2-F-Ph | CH₂CH₂CH₂OH | CH₂ | 1-adamantyl |
|  | bond | Ph | CH₂CMe₂OH | CH₂ | 1-adamantyl |
|  | bond | Ph | CH₂CH₂CONH₂ | CH₂ | 1-adamantyl |

TABLE 6-continued

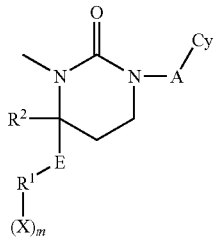

If

| Example No. | E | R¹—(X)$_m$ | R² | A | Cy |
|---|---|---|---|---|---|
| | bond | 4-F-Ph | CH$_2$CH$_2$CH$_2$NHSO$_2$Me | CH$_2$ | 1-adamantyl |
| | bond | 2-F-Ph | CH$_2$CH$_2$CONH$_2$ | CH$_2$ | 1-adamantyl |
| | bond | Ph | CH$_2$CH$_2$N(CH$_2$CH$_2$)$_2$O | CH$_2$ | 1-adamantyl |

TABLE 7

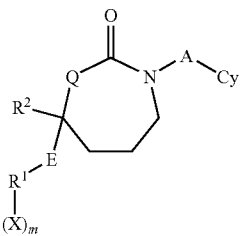

Ig

| Example No. | Q | E-R¹—(X)$_m$ | R² | A | Cy |
|---|---|---|---|---|---|
| PE121 | NH | i-Pr | H | bond | 1-adamantyl |
| PE122 | NH | cyclohexyl | H | bond | 1-adamantyl |
| PE123 | NH | i-Bu | CH$_2$OH | bond | 1-adamantyl |
| PE124 | NH | t-Bu | Me | bond | 1-adamantyl |
| PE125 | NH | i-Pr | H | bond | 2-adamantyl |
| PE126 | NH | cyclohexyl | H | bond | 2-adamantyl |
| PE127 | NH | i-Bu | CH$_2$OH | bond | 2-adamantyl |
| PE128 | NH | t-Bu | Me | bond | 2-adamantyl |
| PE129 | NH | i-Pr | H | bond | 1-adamantyl |
| PE130 | NH | cyclohexyl | H | CH$_2$ | 1-adamantyl |
| PE131 | NH | i-Bu | CH$_2$OH | CH$_2$ | 1-adamantyl |
| PE132 | NH | t-Bu | Me | CH$_2$ | 1-adamantyl |
| PE133 | NMe | i-Pr | H | bond | 1-adamantyl |
| PE134 | NMe | cyclohexyl | H | bond | 1-adamantyl |
| PE135 | NMe | i-Bu | CH$_2$OH | bond | 1-adamantyl |
| PE136 | NMe | t-Bu | Me | bond | 1-adamantyl |
| PE137 | NMe | i-Pr | H | bond | 2-adamantyl |
| PE138 | NMe | cyclohexyl | H | bond | 2-adamantyl |

TABLE 7-continued

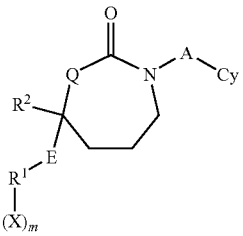

| Example No. | Q | E-R¹—(X)$_m$ | R² | A | Cy |
|---|---|---|---|---|---|
| PE139 | NMe | i-Bu | CH$_2$OH | bond | 2-adamantyl |
| PE140 | NMe | t-Bu | Me | bond | 2-adamantyl |
| PE141 | NMe | i-Pr | H | bond | 1-adamantyl |
| PE142 | NMe | cyclohexyl | H | CH$_2$ | 1-adamantyl |
| PE143 | NMe | i-Bu | CH$_2$OH | CH$_2$ | 1-adamantyl |
| PE144 | NMe | t-Bu | Me | CH$_2$ | 1-adamantyl |
| PE145 | O | i-Pr | H | bond | 1-adamantyl |
| PE146 | O | cyclohexyl | H | bond | 1-adamantyl |
| PE147 | O | t-Bu | Me | bond | 1-adamantyl |
| PE148 | O | i-Pr | H | bond | 2-adamantyl |
| PE149 | O | cyclohexyl | H | bond | 2-adamantyl |
| PE150 | O | t-Bu | Me | bond | 2-adamantyl |
| PE151 | O | i-Pr | H | bond | 1-adamantyl |
| PE152 | O | cyclohexyl | H | CH$_2$ | 1-adamantyl |
| PE153 | O | t-Bu | Me | CH$_2$ | 1-adamantyl |
| PE154 | O | 3-biphenyl | Me | bond | 2-adamantyl |
| PE155 | NH | 4-biphenyl | Me | bond | 2-adamantyl |
| PE156 | O | 3-(3-pyridyl)phenyl | Me | bond | 2-adamantyl |
| PE157 | NH | 3-(1-oxo-4-pyridyl)phenyl | Me | bond | 2-adamantyl |
| PE158 | O | 3-(2-carboxyphenyl)phenyl | Me | bond | 2-adamantyl |
| PE159 | NH | 3-(3-carboxylphenyl)phenyl | Me | bond | 2-adamantyl |
| PE160 | O | 3-(2-methylsulfonyl phenyl)phenyl | Me | bond | 2-adamantyl |
| PE161 | NH | 3-(3-methylsulfonyl phenyl)phenyl | Me | bond | 2-adamantyl |
|  | O | 4-F-Ph | CH$_2$CH$_2$OH | CH$_2$ | 1-adamantyl |
|  | NH | 2-F-Ph | CH$_2$CH$_2$CH$_2$OH | CH$_2$ | 1-adamantyl |
|  | NMe | Ph | CH$_2$CMe$_2$OH | CH$_2$ | 1-adamantyl |
|  | O | Ph | CH$_2$CH$_2$CONH$_2$ | CH$_2$ | 1-adamantyl |
|  | NH | 4-F-Ph | CH$_2$CH$_2$CH$_2$NHSO$_2$Me | CH$_2$ | 1-adamantyl |
|  | NMe | 2-F-Ph | CH$_2$CH$_2$CONH$_2$ | CH$_2$ | 1-adamantyl |
|  | O | Ph | CH$_2$CH$_2$N(CH$_2$CH$_2$)$_2$O | CH$_2$ | 1-adamantyl |
|  | NH | 4-F-Ph | CH$_2$CH$_2$OH | CH$_2$ | 1-adamantyl |
|  | NMe | 2-F-Ph | CH$_2$CH$_2$CH$_2$OH | CH$_2$ | 1-adamantyl |

TABLE 7-continued

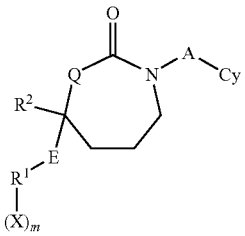

| Example No. | Q | E-R$^1$—(X)$_m$ | R$^2$ | A | Cy |
|---|---|---|---|---|---|
| | O | Ph | CH$_2$CMe$_2$OH | CH$_2$ | 1-adamantyl |
| | NH | Ph | CH$_2$CH$_2$CONH$_2$ | CH$_2$ | 1-adamantyl |
| | NMe | 4-F-Ph | CH$_2$CH$_2$CH$_2$NHSO$_2$Me | CH$_2$ | 1-adamantyl |
| | O | 2-F-Ph | CH$_2$CH$_2$CONH$_2$ | CH$_2$ | 1-adamantyl |
| | O | Ph | CH$_2$CH$_2$N(CH$_2$CH$_2$)$_2$O | CH$_2$ | 1-adamantyl |

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

Biological Assays

The inhibition of purified 11β-HSD1 by compounds of Formula I was measured as follows using a Scintillation Proximity Assay. All reactions were carried out at room temperature in 96 well flexible Microbeta reaction plates. The assay begins by adding 1 microliter of a 0.1 mM solution of a compound of Formula I in DMSO previously diluted in half-log increments (8 points) starting at 1 micromolar final concentration. To this dot was added 50 microliters of substrate solution (50 mM HEPES, pH 7.4, 100 mM KCl, 5 mM NaCl, 2 mM MgCl2 containing 20 microliters of $^3$H cortisone, 1 mM NADPH). After a 10 minute incubation, 50 microliters of enzyme solution containing 20 nM recombinant 11β-HSD1 (expressed in E. coli, and affinity purified) was added, The reaction was incubated for 90 minutes, and stopped by adding 50 microliters of SPA bead mix (18-β-glycyrrhetinic acid, 10 micromolar final, 5 mg/ml protein A coated YSi SPA beads, and 1-microgram/ml alpha-cortisol antibody (East Coast Biologics). The plate shaken for 120 minutes, and the radioactivity corresponding to $^3$H cortisol was measured on a Wallac Microbeta.

The inhibition of microsomal 11β-HSD1 was carried out in the same manner.

The inhibition of 11β-HSD1 by compounds of Formula I in whole cells was measured as follows. Omental adipocytes cultured in 96-well plates were purchased from Zen-Bio, Inc. and used at least two weeks after differentiation from precursor preadipocytes started in medium supplemented with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37 degrees C., 5% CO2 and transferred into serum-free, phenol red free medium for overnight incubation. The assay was performed in a total volume of 200 microliters. The cells were pre-incubated with serum-free, phenol red free medium containing 0.1% (v/v) of DMSO and various concentrations of compounds of Formula I at least 1 h before [$^3$H] cortisone in ethanol (50 Ci/mmol, ARC, Inc.) was added to achieve final concentration of cortisone of 100 nM. The cells were incubated for 3-4 at 37 degrees Centigrade, 5% CO2. Negative controls were incubated without radioactive substrate and received the same amount of [$^3$H] cortisone at the end of the incubation. Formation of [$^3$H] cortisol was monitored by analyzing 25 microliters of each supernatant in scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384),

TABLE 8

| Example | Inhibition of purified 11β-HSD1[a] | Inhibition of microsomal 11β-HSD1[a] | Inhibition of 11β-HSD1 in whole cells[a] |
| --- | --- | --- | --- |
| 1 | ++ | nt | + |
| 2 | ++ | nt | + |
| 3 | + | nt | nt |
| 4 | ++ | nt | ++ |
| 5 | ++ | nt | ++ |
| 6 | + | nt | nt |
| 7 | ++ | nt | + |
| 8 | ++ | nt | ++ |
| 9 | + | nt | nt |
| 10 | + | nt | nt |
| 11 | + | nt | nt |
| 12 | ++ | ++ | ++ |
| 13A | + | nt | nt |
| 13B | − | nt | nt |
| 14 | + | nt | nt |
| 15 | + | nt | nt |
| 16 | ++ | nt | ++ |
| 17 | + | nt | nt |
| 18 | ++ | nt | + |
| 19 | + | nt | nt |
| 20 | ++ | nt | ++ |
| 21 | ++ | nt | ++ |
| 22A | + | nt | nt |
| 22B | + | nt | nt |
| 23 | + | nt | nt |
| 24 | + | nt | nt |
| 25 | ++ | nt | ++ |
| 26 | + | nt | nt |
| 27 | ++ | nt | ++ |
| 28 | ++ | ++ | ++ |
| 29 | nt | ++ | nt |
| 30 | nt | ++ | + |
| 31 | nt | ++ | ++ |
| 32 | nt | ++ | ++ |
| 33 | nt | ++ | ++ |
| 34 | nt | ++ | nt |
| 35 | nt | ++ | nt |
| 36 | nt | + | nt |
| 37 | nt | ++ | + |
| 38 | nt | ++ | nt |

[a]++ means IC$_{50}$ < 50 nM, + means IC$_{50}$ = 50 nM to 1000 nM, − means IC$_{50}$ > 1000 nM, nt means not tested.

The compounds of the invention are useful for ameliorating or treating disorders or diseases in which decreasing the level of cortisol is effective in treating a disease state. Thus, the compounds of the invention can be used in the treatment or prevention of diabetes mellitus, obesity (especially abdominal obesity), symptoms of metabolic syndrome, prothrombotic state, proinflammatory state, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X.

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefore.

The compositions of the invention are 11β-HSD1 inhibitors. Said compositions contain compounds having a mean inhibition constant (IC$_{50}$) against 11β-HSD1 of between about 1,000 nM to about 0.001 nM; preferably between about 50 nM to about 0.001 nM; and more preferably between about 5 nM to about 0.001 nM, The invention includes a therapeutic method for treating or ameliorating an 11β-HSD1 mediated disorder in a subject in need thereof comprising administering to a subject in need thereof an effective amount of a compound of Formula I, or the enantiomers, diastereomers, or salts thereof of composition thereof.

An embodiment of the invention includes administering an 11β-HSD1 inhibiting compound of Formula I or composition thereof alone or in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1 B inhibitors; protein kinase inhibitors (including AMP-activated protein kinase inhibitors); glucagon antagonists, glycogen synthase kinase-3 beta inhibitors; glucose-6-phosphatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

What is claimed is:
1. A compound of the Formula (I)

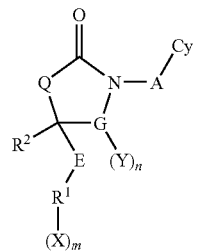

wherein:
$R^1$ is selected from the group consisting of
(1) H; or
(2) $(C_1-C_8)$alkyl, $(C_3-C_7)$cycloalkyl, heterocyclyl, $(C_1-C_4)$alkoxy$(C_1-C_4)$alkyl, $(C_1-C_4)$alkylthio$(C_1-C_4)$alkyl, $(C_1-C_4)$alkylsulfinyl$(C_1-C_4)$alkyl, and $(C_1-C_4)$alkylsulfonyl$(C_1-C_4)$alkyl; or
(3) phenyl, phenyl$(C_1-C_4)$alkyl, heteroaryl, and heteroaryl $(C_1-C_4)$alkyl;
X is independently selected from the group consisting of OH, $CH_2OH$, $(C_1-C_3)$alkyl, $(C_1-C_3)$haloalkyl, OR*, O$((C_1-C_3)$haloalkyl), CN, $CH_2CN$, $NO_2$, $CH_2NO_2$, SH, SR*, $SO_3H$, $CH_2SO_3H$, $SO_2R^*$, $CH_2SO_2R^*$, $SO_2NH_2$, $SO_2NHR^*$, $SO_2NR^*_2$, $CH_2SO_2NH_2$, $CH_2SO_2NHR^*$, $CH_2SO_2NR^*_2$, $SO_2CF_3$, $CH_2SO_2CF_3$, $CONH_2$, $CONHR^*$, $CONR^*_2$, $CH_2CONH_2$, $CH_2CONHR^*$, $CH_2CONR^*_2$, $CO_2H$, $CH_2CO_2H$, $NH_2$, $NHR^*$, $NR^*_2$, $(C_1-C_3)$alkyl$(NH_2)$, $(C_1-C_3)$alkyl$(NHR^*)$, $(C_1-C_3)$alkyl$(NR^*_2)$, aryl, heteroaryl, $SO_3H$, $CH_2SO_3H$ and heterocyclyl optionally substituted with oxo, alkyl, haloalkyl or hydroxyl; and
when $R^1$ heterocyclyl or heteroaryl, X can also be oxo;
m=0, 1, 2 or 3;
$R^2$ is selected from the group consisting of
(1) H; or
(2) $(C_1-C_8)$alkyl, $(C_3-C_7)$cycloalkyl, heterocyclyl, $(C_1-C_4)$alkoxy$(C_1-C_4)$alkyl, $(C_1-C_4)$alkylthio$(C_1-C_4)$alkyl, $(C_1-C_4)$alkylsulfinyl$(C_1-4)$alkyl, and $(C_1-C_4)$alkylsulfonyl$(C_1-C_4)$alkyl each optionally substituted with one to three substituents independently selected from the group consisting of OH, (=O), $CONH_2$, $CO_2H$, $COCH_3$, $C(O)_2CH_3$, $NH_2$, $NHR^*$, $NR^*_2$, aryl, heteroaryl, cyano, OR*, SR*, S(=O)R*, S(=O)$_2R^*$, OP(=O)(OH)$_2$, $NHSO_2R^*$, $NR^*SO_2R^*$, NHC(=O)R*, $NR^*C(=O)R^*$, NHC(=O)OR*, $NR^*C(=O)OR^*$, NHC(=O)$NH_2$, NHC(=O)NHR*, NHC(=O)N$(R^*)_2$, $NR^*C(=O)NH_2$, $NR^*C(=O)NHR^*$, $NR^*C(=O)N(R^*)_2$, OC(=O)$NH_2$, OC(=O)NHR*, OC(=O)N$(R^*)_2$, NHS(=O)$_2OR^*$, $NR^*S(=O)_2OR^*$, NHS(=O)$_2NH_2$, NHS(=O)$_2NHR^*$, NHS(=O)$_2N(R^*)_2$, $NR^*S(=O)_2NH_2$, $NR^*S(=O)_2NHR^*$, $NR^*S(=O)_2N(R^*)_2$, OS(=O)$_2NH_2$, OS(=O)$_2NHR^*$, OS(=O)$_2N(R^*)_2$, and heterocyclyl; or
(3) phenyl, phenyl$(C_1-C_4)$alkyl, heteroaryl and heteroaryl $(C_1-C_4)$alkyl each optionally substituted with one to three substituents independently selected from the group consisting of halogen, OH, $CH_2OH$, $(C_1-C_3)$alkyl, $(C_1-C_3)$haloalkyl, OR, O$((C_1-C_3)$haloalkyl), CN, $CH_2CN$, $NO_2$, $CH_2NO_2$, SH, SR*, $SO_3H$, $CH_2SO_3H$, $SO_2R^*$, $CH_2SO_2R^*$, $SO_2NH_2$, $SO_2NHR^*$, $SO_2NR^*_2$, $CH_2SO_2NH_2$, $CH_2SO_2NHR^*$, $CH_2SO_2NR^*_2$, $SO_2CF_3$, $CH_2SO_2CF_3$, $CONH_2$, $CONHR^*$, $CONR^*_2$, $CH_2CONH_2$, $CH_2CONHR^*$, $CH_2CONR^*_2$, $CO_2H$, $CH_2CO_2H$, $NH_2$, $NHR^*$, $NR^*_2$, $(C_1-C_3)$alkyl$(NH_2)$, $(C_1-C_3)$alkyl$(NHR^*)$, $(C_1-C_3)$alkyl$(NR^*_2)$ aryl, heteroaryl, $SO_3H$, and $CH_2SO_3H$;
each R* is independently $C_1-C_3$ alkyl;
provided that
1) $R^1$ and $R^2$ are not both hydrogen when E is a bond;
2) $R^1$ is not hydrogen when m is greater than 0; and
3) the compound of Formula (I) is not a hydrate or solvate;
E is a bond, $CH_2$, CHMe, $CMe_2$, $CH_2CH_2$, $OCH_2$, $OCHMe$, $OCMe_2$, $SCH_2$, $SCHMe$, or $SCMe_2$, provided that O and S are attached to $R^1$;
G is a 1, 2, or 3 carbon alkylene chain;
Y is independently selected from the group consisting of halogen, $(C_1-C_3)$alkyl, $CF_3$, $CONH_2$, $CH_2CONH_2$, $CO_2H$, $CH_2CO_2H$, $(C_1-C_3)$alkylamino$(C_1-C_3)$alkyl and di$(C_1-C_3)$alkyl amino $(C_1-C_3)$alkyl;
n=0, 1, 2 or 3;
A = bond, $CH_2$, CHMe, $CMe_2$, or $CH_2CH_2$;
Cy = $(C_7-C_{12})$bicycloalkyl or $(C_9-C_{12})$tricycloalkyl in which 1-2 carbon atoms are optionally replaced with heteroatoms independently selected from N and O and which is optionally substituted with 1-3 groups independently selected from halogen, cyano, $(C_1-C_3)$alkyl, halo$(C_1-C_3)$alkyl, hydroxy, hydroxy$(C_1-C_3)$alkyl, amino, $(C_1-C_4)$acylamino, $(C_1-C_3)$alkylsulfonylamino, $CH_2CH_2CO_2H$, $(C_1-C_3)$alkylcarbamoyl, di$(C_1-C_3)$alkylcarbamoyl, $(C_1-C_3)$alkylaminosulfonyl, di$(C_1-C_3)$alkylaminosulfonyl, aralkyl, aryl, heteroaryl, oxo-substituted heteroaryl, amino-substituted heteroaryl, heterocyclyl, oxo-substituted heterocyclyl, C(=NOH)$NH_2$, CON$(R^4)_2$, $CH_2CON(R^4)_2$, $SO_2N(R^4)_2$, $CO_2R^4$, $CH_2CO_2R^4$, $SO_2R^4$, $NR^4COR^4$, $NR^4CO_2R^4$, $NR^4SO_2R^4$ and OC(=O)N$(R^4)_2$,
wherein each $R^4$ is independently hydrogen, $(C_1-C_{10})$alkyl, aryl or aralkyl;

or an enantiomer, diastereomer, or pharmaceutically acceptable salt thereof.

2. The compound of claim 1 wherein:
R$^1$ is selected from the group consisting of
(1) H; or
(2) (C$_1$-C$_8$)alkyl, (C$_3$-C$_7$)cycloalkyl, heterocyclyl, (C$_1$-C$_4$) alkoxy(C$_1$-C$_4$)alkyl, (C$_1$-C$_4$)alkylthio(C$_1$-C$_4$)alkyl, (C$_1$-C$_4$)alkylsulfinyl(C$_1$-C$_4$)alkyl, and (C$_1$-C$_4$)alkylsulfonyl(C$_1$-C$_4$)alkyl; or
(3) phenyl, phenyl(C$_1$-C$_4$)alkyl, heteroaryl, and heteroaryl (C$_1$-C$_4$)alkyl;
X is independently selected from the group consisting of OH, CH$_2$OH, (C$_1$-C$_3$)alkyl, (C$_1$-C$_3$)haloalkyl, OR, O((C$_1$-C$_3$)haloalkyl), CN, CH$_2$CN, NO$_2$, CH$_2$NO$_2$, SH, SR*, SO$_2$H, CH$_2$SO$_2$H, SO$_2$R*,CH$_2$SO$_2$R*, SO$_2$NH$_2$, SO$_2$NHR*, SO$_2$NR*$_2$, CH$_2$SO$_2$NH$_2$, CH$_2$SO$_2$NHR*, CH$_2$SO$_2$NR*$_2$, SO$_2$CF$_3$, CH$_2$SO$_2$CF$_3$, CONH$_2$, CONHR*, CONR*$_2$, CH$_2$CONH$_2$, CH$_2$CONHR*, CH$_2$CONR*$_2$, CO$_2$H, CH$_2$CO$_2$H, NH$_2$, NHR*, NR*$_2$, (C$_1$-C$_3$)alkyl(NH$_2$), (C$_1$-C$_3$)alkyl(NHR*), (C$_1$-C$_3$)alkyl(NR*$_2$), aryl and heteroaryl;
m=0, 1, 2 or 3;
R$^2$ is selected from the group consisting of
(1) H; or
(2) (C$_1$-C$_8$)alkyl, (C$_3$-C$_7$)cycloalkyl, heterocyclyl, (C$_1$-C$_4$) alkoxy(C$_1$-C$_4$)alkyl, (C$_1$-C$_4$)alkylthio(C$_1$-C$_4$)alkyl, (C$_1$-C$_4$)alkylsulfinyl(C$_1$-C$_4$)alkyl, and (C$_1$-C$_4$)alkylsulfonyl(C$_1$-C$_4$)alkyl each optionally substituted with one to three substituents independently selected from the group consisting of OH, (=O), CONH$_2$, CO$_2$H, COCH$_3$, C(O)$_2$CH$_3$, NH$_2$, NHR*, NR*$_2$, aryl and heteroaryl; or
(3) phenyl, phenyl(C$_1$-C$_4$)alkyl, heteroaryl and heteroaryl (C$_1$-C$_4$)alkyl each optionally substituted with one to three substituents independently selected from the group consisting of halogen, OH, CH$_2$OH, (C$_1$-C$_3$) alkyl, (C$_1$-C$_3$)haloalkyl, OR, O((C$_1$-C$_3$)haloalkyl), CN, CH$_2$CN, NO$_2$, CH$_2$NO$_2$, SH, SR*, SO$_2$H, CH$_2$SO$_2$H, SO$_2$R*,CH$_2$SO$_2$R*, SO$_2$NH$_2$, SO$_2$NHR*, SO$_2$NR*$_2$, CH$_2$SO$_2$NH$_2$, CH$_2$SO$_2$NHR*, CH$_2$SO$_2$NR*$_2$, SO$_2$CF$_3$, CH$_2$SO$_2$CF$_3$, CONH$_2$, CONHR*, CONR*$_2$, CH$_2$CONH$_2$, CH$_2$CONHR*, CH$_2$CONR*$_2$, CO$_2$H, CH$_2$CO$_2$H, NH$_2$, NHR*, NR*$_2$, (C$_1$-C$_3$)alkyl(NH$_2$), (C$_1$-C$_3$)alkyl(NHR*), (C$_1$-C$_3$)alkyl(NR*$_2$) aryl and heteroaryl;
each R* is independently C$_1$-C$_3$ alkyl;
provided that
1) R$^1$ and R$^2$ are not both hydrogen when E is a bond;
2) R$^1$ is not hydrogen when m is greater than 0; and
3) the compound of Formula (I) is not a hydrate or solvate;
E is a bond, CH$_2$, CHMe, CMe$_2$, CH$_2$CH$_2$, OCH$_2$, OCHMe, OCMe$_2$, SCH$_2$, SCHMe, or SCMe$_2$, provided that O and S are attached to R$^1$;
G = a 1, 2, or 3 carbon alkylene chain;
Y is independently selected from the group consisting of halogen, (C$_1$-C$_3$)alkyl, CF$_3$, CONH$_2$, CH$_2$CONH$_2$, CO$_2$H, CH$_2$CO$_2$H, (C$_1$-C$_3$)alkylamino(C$_1$-C$_3$)alkyl and di(C$_1$-C$_3$)alkyl amino (C$_1$-C$_3$)alkyl;
n = 0, 1, 2 or 3;
A = bond, CH$_2$, CHMe, CMe$_2$, or CH$_2$CH$_2$;
Cy = (C$_7$-C$_{12}$)bicycloalkyl or (C$_9$-C$_{12}$)tricycloalkyl in which 1-2 carbon atoms are optionally replaced with heteroatoms independently selected from N and O and which is optionally substituted with 1 - 3 groups independently selected from halogen, cyano, (C$_1$-C$_3$)alkyl, halo(C$_1$-C$_3$)alkyl, hydroxy, hydroxy(C$_1$-C$_3$)alkyl, amino, (C$_1$-C$_4$)acylamino, (C$_1$-C$_3$)alkylsulfonylamino, CH$_2$CH$_2$CO$_2$H, (C$_1$-C$_3$)alkylcarbamoyl, di(C$_1$-C$_3$) alkylcarbamoyl, (C$_1$-C$_3$)alkylaminosulfonyl, di(C$_1$-C$_3$) alkylaminosulfonyl, aralkyl, aryl, heteroaryl, oxo-substituted heteroaryl, amino-substituted heteroaryl, heterocyclyl, oxo-substituted heterocyclyl C(=NOH) NH$_2$, CON(R$^4$)$_2$, CH$_2$CON(R$^4$)$_2$, SO$_2$N(R$^4$)$_2$, CO$_2$R$^4$, CH$_2$CO$_2$R$^4$, SO$_2$R$^4$, NR$^4$COR$^4$, NR$^4$CO$_2$R$^4$, and NR$^4$SO$_2$R$^4$,
wherein each R$^4$ is independently hydrogen, (C$_1$-C$_{10}$) alkyl, aryl or aralkyl;
or an enantiomer, diastereomer, or pharmaceutically acceptable salt thereof.

3. The compound of claim 1 wherein R$^1$ is (C$_1$-C$_6$)alkyl, (C$_3$-C$_7$)cycloalkyl or phenyl, R$^2$ is Me, G(Y)$_n$ is CH$_2$ or CH$_2$CH$_2$ and Cy is 1--adamantyl, 2-adamantyl, 1-hydroxy-4-adamantyl, 1-hydroxymethyl-4-adamantyl, or 1-carbamoyl-4-adamantyl.

4. The compound of claim 1, wherein n is 0, and E is a bond.

5. The compound of claim 4, wherein R$^1$ is tert-butyl.

6. The compound of claim 1, wherein:
E is a bond, CH$_2$, CHMe, CMe$_2$, or CH$_2$CH$_2$;
R$^1$ is H, (C$_1$-C$_8$)alkyl, (C$_3$-C$_7$)cycloalkyl, phenyl, phenyl (C$_1$-C$_4$)alkyl, heteroaryl or heteroaryl(C$_1$-C$_4$)alkyl;
X is CN, OH, (C$_1$-C$_3$)alkyl, halo(C$_1$-C$_3$)alkyl, (C$_1$-C$_3$) alkoxy, (C$_1$-C$_3$)alkylsulfonyl, or CONH$_2$;
m is 0, 1, 2 or 3;
R$^2$ is H, Me, or CH$_2$OH;
provided that
1) R$^1$ and R$^2$ are not both hydrogen when E is a bond;
2) R$^1$ is not hydrogen when m is greater than 0; and
3) the compound of Formula (I) is not a hydrate or solvate;
G(Y)$_n$ is CH$_2$, CH(C$_1$-C$_3$)alkyl, C((C$_1$-C$_3$)alkyl)$_2$, or CH$_2$CH$_2$;
A is a bond, or CH$_2$;
Cy is (C$_7$-C$_{12}$)bicycloalkyl or (C$_9$-C$_{12}$)tricycloalkyl in which 1-2 carbon atoms are optionally replaced with heteroatoms independently selected from N and O, and which is optionally substituted with 1 - 3 groups independently selected from halogen, cyano, (C$_1$-C$_3$)alkyl, halo(C$_1$-C$_3$)alkyl, hydroxy, hydroxy(C$_1$-C$_3$)alkyl, amino, (C$_1$-C$_4$)acylamino, (C$_1$-C$_3$)alkylsulfonylamino, CH$_2$CH$_2$CO$_2$H, (C$_1$-C$_3$)alkylcarbamoyl, di(C$_1$-C$_3$) alkylcarbamoyl, (C$_1$-C$_3$)alkylaminosulfonyl, di(C$_1$-C$_3$) alkylaminosulfonyl, optionally substituted aryl, optionally substituted heteroaryl, oxo-substituted heteroaryl, amino-substituted heteroaryl, heterocyclyl, oxo-substituted heterocyclyl, C(=NOH)NH$_2$, CON(R$^4$)$_2$, CH$_2$CON(R$^4$)$_2$, SO$_2$N(R$^4$)$_2$, CO$_2$R$^4$, CH$_2$CO$_2$R$^4$, SO$_2$R$^4$, NR$^4$COR$^4$, NR$^4$CO$_2$R$^4$, and NR$^4$SO$_2$R$^4$,
wherein R$^4$ is hydrogen, (C$_1$-C$_{10}$) alkyl, aryl or aralkyl;
or an enantiomer, diastereomer, or pharmaceutically acceptable salt thereof.

7. The compound of claim 6 wherein Cy is 1-adamantyl, 2-adamantyl, 1-hydroxy-3-adamantyl, 1-(hydroxymethyl)-3-adamantyl, 1-carbamoyl-3-adamantyl, 1-hydroxy-4-adamantyl, 1-(hydroxymethyl)-4-adamantyl, 1-carbamoyl-4-adamantyl, 1-bicyclo[2.2.2]octyl, 1-carbamoyl-4-bicyclo[2.2.2]octyl, 9-bicyclo[3.3.1]nonyl or 3-carbamoyl-9-bicyclo[3.3.1]nonyl.

8. The compound of claim 6, wherein E is a bond or methylene; R$^1$ is H, (C$_1$-C$_8$)alkyl, or (C$_3$-C$_7$)cycloalkyl; X is OH; m is 0 or 1; R$^2$ is H, Me, or CH$_2$OH; G(Y)$_n$ is CH$_2$, CHCH$_3$, or CH$_2$CH$_2$; A is a bond or methylene; and Cy is 1-adamantyl, 2-adamantyl, 1-hydroxy-4-adamantyl, 1-hydroxymethyl-4-adamantyl, or 1-carbamoyl-4-adamantyl.

9. The compound of claim 1, wherein E is a bond; R$^1$ is phenyl; and
m is 0, 1, or 2.

10. The compound of claim 1, wherein E is a bond; R$^1$ is phenyl; X is monoflurophenyl or diflurophenyl; and m is 1.

11. The compound of claim 1, wherein E is a bond; R$^1$ is phenyl; X is pyridyl optionally substituted with alkyl, alkoxy, thioalkoxy, alkylsulfonyl, halogen, trifluoromethyl, dialkylamino, nitro, cyano, CO$_2$H, CONH$_2$, N-monoalkyl-substituted amido or N,N-dialkyl-substituted amido, or by oxo or X is an oxo-substituted heterocyclyl optionally further substituted with alkyl, haloalkyl or hydroxy; and m is 1.

12. The compound of claim 1, wherein $R_2$ is hydroxy($C_2$-$C_5$)alkyl, ω-$H_2NC(=O)(C_1$-$C_3$)alkyl, ω-$MeSO_2NH(C_1$-$C_3$)alkyl or 2-(4-morpholino)ethyl.

13. A compound selected from the group consisting of:
(S)-3-((1-adamantyl)methyl)-5-phenyloxazolidin-2-one;
(S)-3-((1-adamantyl)methyl)-5-isobutyloxazolidin-2-one;
(S)-3-(1- adamantyl)-54 sobutyloxaz olidin-2-one;
(S)-3-(2- adamantyl)-54 sobutyloxaz olidin-2-one;
(S)-3-((1-adamantyl)methyl)-5-(2-chlorophenyl)oxazolidin-2-one;
(S)-3-((1-adamantyl)methyl)-5-(t-butyl)oxazolidin-2-one;
(S)-3-(2-adamantyl)-5-tert-butylox azolidin-2-one ;
(S)-3-(2-adamantyl)-5-methyl-5-phenyloxaz olidin-2-one;
(S)-3-((1-adamantyl)methyl)-5-cyclohexyloxaz olidin-2-one;
(S)-3-(2-adamantyl)-5-cyclohexyloxazolidin-2-one;
(R)-3-(2-adamantyl)-5-cyclohexyloxazolidin-2-one;
(4R,5S)-3-((1-adamantyl)methyl)-4-methyl-5-phenyloxazolidin-2-one;
(S)-1-(2-adamantyl)-4-tert-butylimidazolidin-2-one;
(S)-1-(2-adamantyl)-3-methyl-4-tert-butyl-imidazolidin-2-one;
5-(4-bromophenyl)-3-(2-adamantyl)oxazolidin-2-one;
(S)-1-(1-adamantyl)-4-phenylimidazolidin-2-one;
4-tert-butyl-1-(2-adamantyl)tetrahydropyrimidin-2(1H)-one;
(S)-4-cyclohexyl-1-(2-adamantyl)imidazolidin-2-one;
(S)-4-isopropyl-1-(2-adamantyl)imidazolidin-2-one;
5-(3-bromophenyl)-3-(2-adamantyl)oxazolidin-2-one;
1-(2-adamantyl)-4-(hydroxymethyl)-4-isobutylimidazolidin-2-one:,
5-(biphenyl-3-yl)-3-(2-adamantyl)oxazolidin-2-one; and
5-(biphenyl-4-yl)-3-(2-adamantyl)oxazolidin-2-one; or an enantiomer, diastereomer or pharmaceutically acceptable salts thereof,wherein said compounds are not hydrates or solvates.

14. A pharmaceutical composition comprising a compound of claim 1 or a pharmaceutically acceptable salt thereof in a pharmaceutically acceptable carrier.

15. A method of inhibiting 11β-HSD1 comprising administering to a mammal a compound of claim 1 or a pharmaceutically acceptable salt thereof.

* * * * *